US008815813B2

(12) United States Patent
Bodie

(10) Patent No.: US 8,815,813 B2
(45) Date of Patent: Aug. 26, 2014

(54) METHODS FOR TREATING IMMUNE-MEDIATED DENGUE FEVER INFECTIONS AND ANTIBODY-DEPENDENT ENHANCEMENT OF DENGUE FEVER INFECTIONS, INCLUDING DENGUE HEMORRHAGIC FEVER AND DENGUE SHOCK SYNDROME

(75) Inventor: Neil M. Bodie, Agoura Hills, CA (US)

(73) Assignee: Trinity Therapeutics, Inc., Agoura Hills, CA (US)

( * ) Notice: Subject to any disclaimer, the term of this patent is extended or adjusted under 35 U.S.C. 154(b) by 317 days.

(21) Appl. No.: 13/054,738

(22) PCT Filed: Jul. 17, 2009

(86) PCT No.: PCT/US2009/050966
§ 371 (c)(1),
(2), (4) Date: May 24, 2011

(87) PCT Pub. No.: WO2010/009380
PCT Pub. Date: Jan. 21, 2010

(65) Prior Publication Data
US 2011/0218157 A1    Sep. 8, 2011

Related U.S. Application Data

(60) Provisional application No. 61/081,943, filed on Jul. 18, 2008.

(51) Int. Cl.
| A61K 38/10 | (2006.01) |
| C07K 7/08 | (2006.01) |
| C07K 7/00 | (2006.01) |
| C07K 16/10 | (2006.01) |

(52) U.S. Cl.
CPC . A61K 38/10 (2013.01); C07K 7/08 (2013.01); C07K 7/00 (2013.01); C07K 16/1081 (2013.01)
USPC ............................................. 514/21.4

(58) Field of Classification Search
CPC ............ A61K 38/10; C07K 7/08; C07K 7/00; C07K 16/1081
USPC ............................................. 514/21.4
See application file for complete search history.

(56) References Cited

U.S. PATENT DOCUMENTS

| 4,383,317 | A | 5/1983 | Haville |
| 5,189,014 | A | 2/1993 | Cowan, Jr. et al. |
| 5,693,758 | A | 12/1997 | Gould et al. |
| 5,821,337 | A | 10/1998 | Carter et al. |
| 5,932,483 | A | 8/1999 | Baumann et al. |
| 6,319,897 | B1 | 11/2001 | Lambris et al. |
| 6,355,683 | B1 | 3/2002 | Baell et al. |
| 6,818,611 | B1 | 11/2004 | Altman |
| 6,916,904 | B2 | 7/2005 | Bodie et al. |
| 7,122,516 | B2 | 10/2006 | Altman |
| 7,205,382 | B2 | 4/2007 | Ronspeck et al. |
| 7,365,162 | B2 | 4/2008 | Altman |
| 7,714,104 | B2 | 5/2010 | Bodie et al. |
| 7,786,258 | B2 | 8/2010 | Bodie et al. |
| 2002/0146428 | A1 | 10/2002 | Hultgren et al. |
| 2003/0204050 | A1 | 10/2003 | Bodie et al. |
| 2004/0087765 | A1 | 5/2004 | Ronspeck et al. |
| 2004/0253247 | A1 | 12/2004 | Dennis et al. |
| 2005/0148030 | A1 | 7/2005 | Bodie et al. |
| 2006/0099571 | A1 | 5/2006 | Altman |
| 2007/0225231 | A1 | 9/2007 | Bodie et al. |
| 2007/0276125 | A1 | 11/2007 | Bodie et al. |
| 2008/0187490 | A1 | 8/2008 | Bodie et al. |
| 2008/0200392 | A1 | 8/2008 | Bodie et al. |
| 2008/0207498 | A1 | 8/2008 | Bodie et al. |
| 2009/0105138 | A1 | 4/2009 | Bodie et al. |
| 2010/0113362 | A1 | 5/2010 | Bodie et al. |
| 2011/0218157 | A1 | 9/2011 | Bodie et al. |
| 2012/0021988 | A1 | 1/2012 | Bodie et al. |
| 2012/0115791 | A1 | 5/2012 | Bodie et al. |
| 2013/0130987 | A1 | 5/2013 | Bodie et al. |

FOREIGN PATENT DOCUMENTS

| EP | 0097994 | 9/1987 |
| EP | 0098829 | 5/1989 |
| WO | WO 98/26794 | 6/1998 |
| WO | WO 00/22112 | 4/2000 |
| WO | WO 01/45746 | 6/2001 |
| WO | WO 02/38592 | 5/2002 |
| WO | WO 03/091395 | 11/2003 |
| WO | WO03104459 A1 | 12/2003 |

(Continued)

OTHER PUBLICATIONS

Definition of derivative from http://cancerweb.ncl.ac.uk/omd/about. html, pp. 1-5, Accessed Jul. 7, 2005.*
Abdul-Majid et al., "Fc receptors are critical for autoimmune inflammatory damage to the central nervous system in experimental autoimmune encephalomyelitis," Scand. J.Immunol., 2002, 55:70-81.
Abeliovich et al., "Mice lacking α-synuclein display functional deficits in the nigrostriatal dopamine system," Neuron, 2000, 25:239-252.
Agnello et al., "C1q precipitins in the sera of patients with systemic lupus erythematosus and other hypocomplementemic states: Characterization of high and low molecular weight types," J. Exp. Med., 1971, 134(3):228-241.

(Continued)

Primary Examiner — Julie Ha
(74) Attorney, Agent, or Firm — Fish & Richardson P.C.

(57) ABSTRACT

Polypeptides and other compounds that can bind specifically to the $C_H2$-$C_H3$ cleft of an immunoglobulin molecule, as well as methods for using such polypeptides and compounds to inhibit Fc-mediated immune complex formation in viral infection, are described. For example, polypeptides and other compounds can be used to inhibit binding of DF-associated, immune-complexed IgG anti-DF viron(s) or DV viral antigens to FγR, ADE of DF/DHF/DSS infections by inhibition of DF viral antigen binding to immune complexed IgG, FγR and immune complexed IgG mC1q (membrane C1q) or soluble C1q binding.

6 Claims, No Drawings

(56) References Cited

FOREIGN PATENT DOCUMENTS

| WO | WO 2004/011485 | 2/2004 |
|---|---|---|
| WO | WO2004058747 A1 | 7/2004 |
| WO | WO 2005/086947 | 9/2005 |
| WO | WO2006020930 A2 | 2/2006 |
| WO | WO 2007/030475 | 3/2007 |
| WO | WO 2007/068047 | 6/2007 |
| WO | WO2009023777 A2 | 2/2009 |

OTHER PUBLICATIONS

Agnello et al., "Precipitin reactions of the C1q component of complement with aggregated γ-globulin and immune complexes in gel diffusion," *Immunol.*, 1970, 19:909-919.

Alexianu et al., "Immune reactivity in a mouse model of familial ALS correlates with disease progression," *Neurol.*, 2001, 57:1282-1289.

Alim et al., "Demonstration of a role for α-synuclein as a functional microtubule-associated protein," *J. Alzheimer's Dis.*, 2004, 6:435-442.

Anderson et al. "Anti-GPIIb/IIIa (CD41) monoclonal antibodyinduced platelet activation requires Fc receptor- dependent cell-cell interaction," *Br. J. Haematol.*, 1991, 79:75-83.

Anderson et al., "The Fc receptor for immunoglobulin G (Fc gamma RII) on human platelets," *Semin. Thromb. Hemost.*, 1995, 21:1-9.

Appel et al., "Immunoglobulins from animals models of motor neuron disease and from human amyotrophic lateral sclerosis patients passively transfer physiological abnormalities to the neuromuscular junction," *Proc. Natl. Acad. Sci. USA*, 1991, 88:647-651.

Artandi et al., "Monoclonal IgM rheumatoid factors bind IgG at a discontinuous epitope comprised of amino acid loops from heavy-chain constant-region domains 2 and 3," *Proc. Natl. Acad. Sci. USA*, 1992, 89:94-98.

Åsbakk et al., "An antigenic determinant is shared by psoriasis-associated p27 antigen and the Fc part of human IgG," *APMIS*, 1991, 99:551-556.

Balestrieri et al., "Inhibitory effect of IgM rheumatoid factor on immune complex solubilization capacity and inhibition of immune precipitation," *Arthritis Rheum.*, 1984, 27(10):1130-1136.

Banci et al., "Fully metallated S134N Cu,Zn-superoxide dismutase displays abnormal mobility and intermolecular contacts in solution," *J. Biol. Chem.*, 2005, 280(43):35815-35821.

Banci et al., "Human SOD1 before harboring the catalytic metal. solution structure of copper-depleted, disulfide-reduced form" *J. Biol. Chem.*, 2006, 281(4):2333-2337.

Banci et al., "The solution structure of reduced dimeric copper zinc superoxide dismutase. The structural effects of dimerization," *Eur. J. Biochem.*, 2002, 269:1905-1915.

Betz et al., "De novo design of native proteins: characterization of proteins intended to fold into antiparallel, Rop-like, four-helix bundles," *Biochem.*, 1997, 36:2450-2458.

Blanchette et al., "Management of chronic immune thrombocytopenic purpura in children and adults," *Semin. Hematol.*, 1998, 35:36-51.

Blom et al., "Fcγr expression on macrophages is related to severity and chronicity of synovial inflammation and cartilage destruction during experimental immune-complex-mediated arthritis (ICA)," *Arthritis Res.*, 2000, 2:489-503.

Bonelli et al., "Solid phase synthesis of retro-inverso peptide analogues," *Int. J. Peptide Protein Res.*, 1984, 24:553-556.

Boren and Gershwin, "Inflamm-aging: autoimmunity, and the immune-risk phenotype," *Autoimmunity Rev.*, 3:401-406, 2004.

Bouras et al., "Humoral immunity in brain aging and Alzheimer's disease," *Brain Research Reviews*, 2005, 48:477-487.

Bouras et al., "Induction of MC-I immunoreactivity in axons after injection of the Fc fragment of human immunoglobulins in macaque monkeys," *Acta Neuropathol.*, 2003, 105:58-64.

Bruijn et al., "Aggregation and motor neuron toxicity of an ALS-Linked SOD1 mutant independent from wild-type SOD1," *Science*, 1998, 281:1851-1854.

Bruijn et al., "ALS-linked SOD1 mutant G85R mediates damage to astrocytes and promotes rapidly progressive disease with SOD1-containing inclusions," *Neuron*, 1997, 18:327-338.

Bruijn et al., "Unraveling the mechanisms involved in motor neuron degeneration in ALS," *Annu. Rev. Neurosci.*, 2004, 27:723-749.

Cassel et al., "Differential expression of FcRIIA, FcRIIB, and FcRIIC in hematopoietic cells: analysis of transcripts ," *Mol. Immunol.*, 1993, 30:451-460.

Check, "Nerve inflammation halts trial for Alzheimer's drug," *Nature*, 2002, 415:462.

Chen et al., "Experimental destruction of substantia nigra initiated by Parkinson disease immunoglobulins," *Arch. Neurol.*, 1998, 55:1075-1080.

Cleveland, "From charcot to SOD1: mechanisms of selective motor neuron death in ALS," *Neuron*, 1999, 24:515-520.

Clot et al., "Immunological aspects of psoriasis. III Fc-γ-receptor bearing mononuclear cells in peripheral blood," *Brit. J. Derm.*, 1978, 99:25-30.

Clynes et al., "Fc receptors are required in passive and active immunity to melanoma," *Proc. Natl. Acad. Sci. USA*, 1998, 95:652-656.

Clynes et al., "Inhibitory Fc receptors modulate in vivo cytoxicity against tumor targets," *Nat. Med.*, 2000, 6(4):443-446.

Clynes et al., "Uncoupling of immune complex formation and kidney damage in autoimmune glomerulonephritis," *Science*, 1998, 279:1052-1054.

Clynes and Ravetch, "Cytotoxic antibodies trigger inflammation through Fc receptors," *Immunity*, 1995, 3:21-26.

Clynes, "Immune complexes as therapy for autoimmunity," *J Clin Invest.*, 2005, 115(1):25-27.

Cochran, "Antagonists of protein-protein interactions," *Chemistry & Biology*, 2000, 7:R85-R94.

Cochran, "Protein-protein interfaces: mimics and inhibitors," *Curr. Opin. Chem. Biol*, 2001, 5:654-659.

Corper et al, "Structure of a human IgM rheumatoid factor Fab bound to its autoantigen IgG Fc reveals a novel topology of antibody-antigen interaction," *Nat Struct Biol.*, 1997, 4:374-381.

Costa et al., "Non-specific binding of heat-aggregated IgG to histone detected by ELISA," *J. Immunol. Meth.*, 1984, 74:283-291.

Couillard-Després et al., "Protective effect of neurofilament heavy chain overexpression in motor neuron disease induced by mutant superoxide dismutase," *Proc. Natl. Acad. Sci. USA*, 1998, 95:9626-9630.

Coxon et al., "FcγRIII mediates neutrophil recruitment to immune complexes: a mechanism for neutrophil accumulation in immune-mediated inflammation," *Immunity*, 2001, 14:693-704.

Coyle and Procyk-Dougherty, "Multiple sclerosis immune complexes: an analysis of component antigens and antibodies," *Ann. Neurol.*, 1984, 16:660-667.

Crow et al., "Superoxide dismutase catalyzes nitration of tyrosines by peroxynitrate in the rod and head domains of neurofilament-L," *J. Neurochem.*, 1997, 69:1945-1953.

Dalaker et al., "Expression of the psoriasis-associated antigen, Pso p27, is inhibited by cyclosporin A," *Acta Derm. Venereol.*, 1999, 79:281-284.

Das et al., "Amyloid-β immunization effectively reduces amyloid deposition in FcRγ-/-knock-out mice," *J. Neurosci.*, 2003, 23(24):8532-8538.

Deckmyn and De Reys, "Functional effects of human antiplatelet antibodies ," *Sem Thromb. Hemost.*, 1995, 21:46-59.

DeLano et al., "Convergent solutions to binding at a protein-protein interface," *Science*, 2000, 287:1279-1283.

Demestre et al., "ALS-IgG-induced selective motor neurone apoptosis in rat mixed primary spinal cord cultures," *J. Neurochem.*, 2005, 94:268-275.

Di Noto et al., "Proteasomal degradation of mutant superoxide dismutases linked to amyotrophic lateral sclerosis," *J. Biol. Chem.*, 2005, 280(48):39907-39913.

DiDonato et al., "ALS mutants of human superoxide dismutase form fibrous aggregates via framework destabilization," *J. Mol. Biol.*, 2003, 332:601-615.

Dodel et al., "Intravenous immunoglobulins containing antibodies against beta-amyloid for the treatment of Alzheimer's disease," *J Neurol Neurosurg Psychiatry.*, 75(10):1472-1474, 2004.

(56) References Cited

OTHER PUBLICATIONS

Doucette et al., "Dissociation of human copper-zinc superoxide dismutase dimers using chaotrope and reductant," *J. Biol. Chem.*, 2004, 279(52):54558-54566.

Duchen, "Contributions of mitochondria to animal physiology: from homeostatic sensor to calcium signaling and cell death," *J. Physiol.*, 1999, 516:1-17.

Durand et al., "Early abnormalities in transgenic mouse models of amyotrophic lateral sclerosis," *J. Physiol.*, 2006, 99:211-220.

Easterbrook-Smith et al., "The role of Fc:Fc interactions in insoluble immune complex formation and complement activation," *Mol. Immunol.*, 1988, 25(12):1331-1337.

Elam et al., "An alternative mechanism of bicarbonate-mediated peroxidation by copper-zinc superoxide dismutase," *J. Biol. Chem.*, 2003, 278(23):21032-21039.

Elmgreen et al., "Demonstration of circulating immune complexes by the indirect leucocyte phagocytosis test in chronic inflammatory bowel disease," *Acta Med. Scan.*, 1985, 218:73-78.

Engelhardt et al., "Altered calcium homeostasis and ultrastructure in motoneurons of mice caused by passively transferred anti-motoneuronal IgG," *J. Neuropathol. Exp. Neurol.*, 1997, 56(1):21-39.

Engelhardt et al., "Stereotaxic injection of IgG from patients with Alzheimer disease initiates injury of cholinergic neurons of the basal forebrain," *Arch. Neurol.*, 2000, 57:681-686.

Engelhardt et al., "Subcellular localization of IgG from the sera of ALS patients in the nervous system," *Acta Neurol. Scand.*, 2005, 112:126-133.

Ezaki et al., "Human monoclonal rheumatoid factors augment arthritis in mice by the activation of T cells," *Clin. Exp. Immunol.*, 1996, 104:474-482.

Ferraroni et al., "The crystal structure of the monomeric human SOD mutant F50E/G51E/E133Q at atomic resolution. The enzyme mechanism revisited," *J. Mol. Biol.*, 1999, 285:413-426.

Ferri et al., "Cell death in amyotrophic lateral sclerosis: interplay between neuronal and glial cells," *FASEB J.*, 2004, 18(11):1261-1263.

Fossati et al., Fcγ receptors in autoimmune diseases,: *Eur. J. Clin. Invest.*, 2001, 31:821-831.

Frangione and Milstein, "Variations in the S-S bridges of immunoglobins G: interchain disulphide bridges of γG3 myeloma proteins," *J. Mol. Biol.*, 1968, 33:893-906.

Fratantoni et al., "Uptake of immunoglobulin G from amyotrophic lateral sclerosis patients by motor nerve terminals in mice," *J. Neurol. Sci.*, 1996, 137:97-102.

Fujiwara et al., "Different immunoreactivity against monoclonal antibodies between wild-type and mutant copper/zinc superoxide dismutase linked to amyotrophic lateral sclerosis," *J. Biol. Chem.*, 2005, 280(6):5061-5070.

Furukawa and O'Halloran, "Amyotrophic lateral sclerosis mutations have the greatest destabilizing effect on the apo- and reduced form of SOD1, leading to unfolding and oxidative aggregation," *J. Biol. Chem.*, 2005, 280(17):17266-17274.

Garcia et al., "Mutations in neurofilament genes are not a significant primary cause of non-SOD1-mediated amyotrophic lateral sclerosis," *Neurobiol. Dis.*, 2006, 21:102-109.

Gergely and Sármay, "Fcγ receptors in malignancies: friends or enemies?" Adv. Cancer Res., 1994, 64:211-245.

Ghetie and Ward, "Multiple roles for the major histocompatibility complex class I-related receptor FcRn," *Ann. Rev. Immunol.*, 2000, 18:739-766.

Girkontaite et al., "Immunochemical study of human immunoglobulin G Fc region," *Cancer Biother. Radiopharm.*, 1996, 11:87-96.

Glader et al., "The proatherogenic properties of lipoprotein(a) may be enhanced through the formation of circulating immune complexes containing *Chlamydia pneumoniae*—specific IgG antibodies," *Eur. Heart J.*, 2000, 21:639-646.

Gómez-Guerrero et al., "Administeration of IgG Fc fragments prevents glomerular injury in experimental immune complex nephritis," *J. Immunol.*, 2000, 164:2092-2101.

Goss et al., "Bicarbonate enhances the peroxidase activity of Cu,Zn-SOD," *J Biol Chem.*, 1999, 274:28233-28239.

Guddat et al., "Local and Transmitted conformational changes on complexation of an anti-sweetener Fab," *J. Mol. Biol.*, 1994, 236:247-274.

Gussin et al., "Effect of circulating immune complexes on the binding of rheumatoid factor to histones," *Ann. Rheum. Dis.*, 2000, 59:351-358.

Gussin et al., "Noncognate binding to histones of IgG from patients with idiopathic systemic lupus erythematosus," *Clin. Immunol.*, 2000, 96(2):150-161.

Haake et al, "The Modificaton of human immunoglobulin binding to staphylococcal protein A using diethylpyrocarbonate," *J Immunol.*, 1982, 129:190.

Hall et al., "Relationship of microglial and astrocytic activation to disease onset and progression in a transgenic model of familial ALS," *GLIA*, 1998, 23:249-256.

Hamano et al., "Immune complex and Fc Receptor-mediated augmentation of antigen presentation for in vivo Th cell responses," *J. Immunol.*, 2000, 164:6113-6119.

Harrington et al., "Demonstration of a thrombocytopenic factor in the blood of patients with thrombocytopenic purpura," *J. Lab. Clin. Med.*, 1951, 38:1-10.

Harris et al., "Refined structure of an intact IgG2a monoclonal antibody," *Biochemistry*, 1997, 36:1581-1597.

Hayward et al., "Decreased metallation and activity in subsets of mutant superoxide dismutases associated with familial amyotrophic lateral sclerosis," *J. Biol. Chem.*, 2002, 277(18):15923-15931.

He et al., "Role of Fcγ receptors in nigral cell injury induced by Parkinson disease immunoglobulin injection into mouse substantia nigra," *Exp. Neurol.*, 2002, 176:322-327.

Henkel et al., "Presence of dendritic cells, MCP-1, and activated microglia/macrophages in amyotrophic lateral sclerosis spinal cord tissue," *Ann. Neurol.*, 2004, 55:221-235.

Henkel et al., "The chemokine MCP-1 and the dendritic and myeloid cells it attracts are increased in the mSOD1 mouse model of ALS," *Mol. Cell. Neurosci.*, 2006, 31(3):427-437.

Hilbush et al., "New prospects and strategies for drug target discovery in neurodegenerative disorders," *NeuroRx*, 2005, 2:627-637.

Hock et al., "Generation of antibodies for beta-amyloid by vaccination of patients with AD," 2002, *Nat Med.*, 8:1270-1275.

Holmdahl et al., "Generation of monoclonal rheumatoid factors after immunization with collagen II-anti-collagen II immune complexes. An anti-idiotypic antibody to anti-collagen II is also a rheumatoid factor," *Scand. J. Immunol.*, 1986, 24:197-203.

Hoover et al., "Modulation of growth and differentiation of murine myeloma cells by immunoglobulin binding factors," *Curr. Top. Microbiol. Immunol.*, 1990, 166:77-85.

Hora et al., "Receptors for IgG complexes activate synthesis of monocyte chemoattractant peptide 1 and colony-stimulating factor 1," *Proc. Natl. Acad. Sci. USA*, 1992, 89:1745-1749.

Hough et al., "Dimer destabilization in superoxide dismutase may result in disease-causing properties: Structures of motor neuron disease mutants," *Proc. Natl. Acad. Sci. USA*, 2004, 101(16):5976-5981.

Hyun et al., "Proteasomal inhibition causes the formation of protein aggregates containing a wide range of proteins, including nitrated proteins," *J Neurochem.*, 2003, 363-373.

Iivanainen,"The significance of abnormal immune responses in patients with multiple sclerosis," *J. Neuroimmunol.*, 1981, 1:141-172.

Indik et al.,"Human Fc gamma RII, in the absence of other Fc gamma receptors, mediates a phagocytic signal," *J. Clin. Invest.*, 1991, 88:1766-1771.

Jaarsma et al., "Human Cu/Zn superoxide dismutase (SOD1) overexpression in mice causes mitochondrial vacuolization, axonal degeneration, and premature motoneuron death and accelerates motoneuron disease in mice expressing a familial amyotrophic lateral sclerosis mutant SOD1," *Neurobiology of Disease*, 2000, 7:623-643.

(56) References Cited

OTHER PUBLICATIONS

Jackson, "Contributions of protein structure-based drug design to cancer chemotherapy," *Seminars in Oncology*, 1997, 24(2):164-172.
Jefferis et al., "Immunogenic and antigenic epitopes of immunoglobulins. VIII. A human monoclonal rheumatoid factor having specificity for a discontinuous epitope determined by histidine/arginine interchange as residue 435 of immunoglobulin G," *Immunol. Lett.*, 1984, 7:191-194.
Jones et al., "Structure-based design of lipophilic quinazoline inhibitors of thymidylate synthase," *J. Med. Chem.*, 1996, 39:904-917.
Jonsson et al., "Minute quantities of misfolded mutant superoxide dismutase-1 cause amyotrophic lateral sclerosis," *Brain*, 2004, 127:73-88.
Kabat et al., *Sequences of Proteins of Immunological Interest*, 5th Edition, Public Health Service, U.S. Department of Health and Human Services, Bethesda, MD, [Table of Contents] 11 pages, 1991.
Kabat et al., *Sequences of Proteins of Immunological Interest*, Fourth Edition, 1987, U.S. Department of Health and Human Services, Public Health Service National Institutes of Health, [Table of Contents] 4 pages, 1987.
Khare et al., "The rate and equilibrium constants for a multistep reaction sequence for the aggregation of superoxide dismutase in amyotrophic lateral sclerosis," *Proc. Natl. Acad. Sci. USA*, 2004, 101(42):15094-15099.
Kim et al., "Oxidative modification of neurofilament-L by the Cu,Zn-superoxide dismutase and hydrogen peroxide system," *Biochimie*, 2004, 86:553-559.
Kitazawa et al., "Microglia as a potential bridge between the amyloid b-peptide and tau," *Ann NY Acad. Sci.*, 2004, 1035:85-103.
Kleinau et al., "Induction and Suppression of collagen-induced arthritis is dependent on distinct Fcγ receptors," *J. Exp. Med.*, 2000, 191(9):1611-1616.
Kong and Xu, "Massive mitochondrial degeneration in motor neurons triggers the onset of amyotrophic lateral sclerosis in mice expressing a mutant SOD1," *J. Neurosci.*, 1998, 18(9):3241-3250.
Koroleva et al., "Binding of complement subcomponent C1q to *Streptococcus pyogenes*: evidence for interactions with the M5 and FcRA76 proteins," *FEMS Immunol. Med. Microbiol.*, 1998, 20:11-20.
Kotz et al., "Phage-display as a tool for quantifying protein stability determinants," *Eur. J. Biochem.*, 2004, 271:1623-1629.
Kowall et al., "In vivo neurotoxicity of beta-amyloid [β(1-40)] and the β(25-35) fragment," *Neurobiol of Aging*, 1992, 13:537-542.
Kuo et al., "Hyperexcitability of cultured spinal motoneurons from presymptomatic ALS mice," *J. Neurophysiol.*, 2004, 91:571-575.
Kuruvilla et al., "Dengue virus infection and immune response in humanized RAG2$^{-/-}$γc$^{-/-}$ (RAG-hu) mice," *Virol.*, 2007, 369:143-152.
Landsbury Jr., "Back to the future: the 'old-fashioned' way to new medications for neurodegeneration," *Nat. Rev Neurosci.*, 2004, S51-S57.
Le et al., "Microglial activation and dopaminergic cell injury: an in vitro model relevant to Parkinson's disease," *J. Neurosci.*, 2001, 21(21):8447-8455.
Leach et al., "Isolation from human placenta of the IgG transporter, FcRn, and localization to the syncytiotrophoblast," *J. Immunol.*, 1996, 157:3317-3322.
Levy et al., "Protein topology determines binding mechanism," *Proc. Natl. Acad. Sci. USA*, 2004, 101(2):511-516.
Lin et al., "3' Untranslated region in a light neurofilament (NF-L) mRNA triggers aggregation of NF-L and mutant superoxide dismutase 1 proteins in neuronal cells," *J. Neurosci.*, 2004, 24(11):2716-2726.
Lindberg et al., "Folding of human superoxide dimutase: Disulfide reduction prevents dimerization and produces marginally stable monomers," *Proc. Natl. Acad. Sci. USA*, 2004, 101(45):15893-15898.
Lindberg et al., "Systematically perturbed folding patterns of amyotrophic lateral sclerosis (ALS)-associated SOD1 mutants," *Proc. Natl. Acad. Sci. USA*, 2005, 102(28):9754-9759.
Liu et al., "β2-microglobulin-deficient mice are resistant to bullous pemphigoid," *J. Exp. Med.*, 1997, 186(5):777-783.
Lobsiger et al., "Altered axonal architecture by removal of the heavily phosphorylated neurofilament tail domains strongly slows superoxide dismutase 1 mutant-mediated ALS," *Proc. Natl. Acad. Sci. USA*, 2005, 102(29):10351-10356.
Lopez et al, "Acidic pH increases the avidity of FcγR for immune complexes," *Immunology*, 1999,98:450-455.
Lüdemann et al., "O-glycosylation of the tail domain of neurofilament protein M in human neurons and in spinal cord tissue of a rat model of amyotrophic lateral sclerosis (ALS)," *J. Biol. Chem.*, 2005, 280(36):31648-31658.
Manzi et al., "Inflammation-mediated rheumatic diseases and atherosclerosis," *Ann. Rheum. Dis.*, 2000, 59(5):321-325.
Marino et al., "Prevention of systemic lupus erythematosus in MRL/lpr mice by administration of an immunoglobulin-binding peptide," *Nat. Biotechnol.*, 2000, 18:735-739.
Martin et al., "Crystal structure at 2.8 A of an FcRn/heterodimeric Fc complex: mechanism of pH-dependent binding," *Mol. Cell*, 2001, 7:867-877.
Mathiot et al., "In vitro Inhibition of tumor B cell growth by IgG-BF-producing FcγRII+ T Cell hybridoma and by immunoglobulin G-binding factors," *Immunol. Res.*, 1992, 11:296-304.
McCall and Easterbrook-Smith, "The presence of histidine residues at or near the C1q binding site of rabbit immunoglobulin G," *Biochim. Biophys. Acta*, 1987, 912:9-15.
Millecamps et al., "Synaptic sprouting increases the uptake capacities of motoneurons in amyotrophic lateral sclerosis mice," *Proc. Natl. Acad. Sci. USA*, 2001, 98(13):7582-7587.
Mizutani et al., "Development and characterization of monoclonal antiplatelet autoantibodies from autoimmune thrombocytopenic purpura-prone (NZW x BXSB)F1 mice," *Blood*, 1993, 82:837-844.
Mohamed et al., "Immunoglobulin Fcγ receptor promotes immunoglobulin uptake, immunoglobulin-mediated calcium increase, and neurotransmitter release in motor neurons," *J. Neurosci. Res.*, 2002, 69:110-116.
Møller and Christiansen, "Fc-mediated immune precipitation. III. Visualization by electron microscopy," *Immunology*, 1983, 48:469-476.
Møller and Pedersen, "Fc-mediated immune precipitation IV. Antigen dependency and specificity," *Immunology*, 1983, 48:477-488.
Møller and Steensgaard, "Fc-mediated immune precipitation. II. Analysis of precipitating immune complexes by rate-zonal ultracentrifugation," *Immunology*, 1979, 38:641-648.
Møller, "Fc-mediated immune precipitation. I. A new role of the Fc-portion of IgG," *Immunology*, 1979, 38:631-640.
Morrison et al., "Early and selective pathology of light chain neurofilament in the spinal cord and sciatic nerve of G86R mutant superoxide dismutase transgenic mice," *Exp Neurology*, 2000, 165:207-220.
Nardella et al., "IgG rheumatoid factors and staphylococcal protein A bind to a common molecular site on IgG," *J. Exp. Med.*, 1985, 162:1811-1824.
Nardella et al., "T15 group A streptococcal Fc receptor binds to the same location on IgG as staphylococcal protein A and IgG rheumatoid factors," *J. Immunol.*, 1987, 138:922-926.
Nguyen et al., "Exacerbation of motor neuron disease by chronic stimulation of innate immunity in a mouse model of amyotrophic lateral sclerosis," *J. Neurosci.*, 2004, 24(6):1340-1349.
Nielsen et al. "Release of leukotriene B4 and 5-hydroxyeicosatetraenoic acid during phagocytosis of artificial immune complexes by peripheral neutrophils in chronic inflammatory bowel disease," *Clin. Exp. Immunol.*, 1986, 65:465-471.
Obál et al., "Recruitment of activated microglia cells in the spinal cord of mice by ALS IgG," *Neuroreport*, 2001, 12(11):2449-2452.
O'Brien et al, "The effects of histidine residue modifications on the immune precipitating ability of rabbit IgG," *Arch Biochem Biophys.*, 1994, 310:25-31.
Orr et al., "A possible role for humoral immunity in the pathogenesis of Parkinson's disease," *Brain*, 2005, 128:2665-2674.
Padlan, "Anatomy of the antibody molecule," *Mol. Immunol.*, 1994, 31:169-217.

(56) References Cited

OTHER PUBLICATIONS

Pasceri and Yeh, "A tale of two diseases. Atherosclerosis and rheumatoid arthritis," *Circulation*, 1999, 100:2124-2126.
Peress et al., "Identification of FcγRI, II and III on normal human brain ramified microglia and on microglia in senile plaques Alzheimer's disease," *J. Neuroimmunol.*, 1993, 48:71-80.
Petkova et al., "Human antibodies induce arthritis in mice deficient in the low-affinity inhibitory IgG receptor Fc gamma RIIB" *J. Exp. Med.*, 2006, 203(2):275-280.
Poston, "A mechanism for demyelinating disease?" *Lancet*, 1984, 1:1268-1271.
Procaccia et al., "Circulating immune complexes in serum and in cerebrospinal fluid of patients with multiple sclerosis," *Acta Neurol. Scand.*, 1988, 77:373-381.
Procaccia et al., "Detection of rheumatoid factors of different isotypes and of circulating immune complexes in patients with inflammatory bowel disease," *Boll Ist. Sieroter*. Milan, 1990, 69:413-421.
Pullen et al., "Passive transfer of purified IgG from patients with amyotrophic lateral sclerosis to mice results in degeneration of motor neurons accompanied by Ca2+ enhancement," 2004 *Acta Neuropathol.*,107:35-46.
Raghavan and Bjorkman, "Fc receptors and their interactions with immunoglobulins," *Annu Rev Dev Biol.*, 1996, 12:181-220.
Rakhit et al., "Monomeric Cu,Zn-superoxide dismutase is a common misfolding intermediate in the oxidation models of sporadic and familial amyotrophic lateral sclerosis," *J. Biol. Chem.*, 2004, 279(15):15499-15504.
Ratcliffe et al., "Immunocytochemical detection of Fcγ receptors in human atherosclerotic lesions," *Immunol. Lett.*, 2001, 77:169-174.
Ravetch, "A full complement of receptors in immune complex diseases," *J Clin Invest.*, 2002, 110:1759-1761.
Ray and Lansbury, Jr., "A possible therapeutic target for Lou Gehrig's disease," *Proc. Natl. Acad. Sci. USA*, 2004, 101(16):5701-5702.
Riederer et al., "Human immunoglobulins and Fc fragments promote microtubule assembly via tau proteins and induce conformational changes of neuronal microtubules in vitro," *NeuroReport*, 2003, 14:117-121.
Ripps et al., "Transgenic mice expressing an altered murine superoxide dismutase gene provide an animal model of amyotrophic lateral sclerosis," *Proc. Natl. Acad. Sci. USA*, 1995, 92:689-693.
Rødahl et al., "Participation of antigens related to the psoriasis associated antigen, pso p27, in immune complex formation in patients with ankylosing spondylitis," *Ann. Rheum. Dis.*, 1988, 47:628-633.
Rodriguez et al., "Destabilization of apoprotein in insufficient to explain Cu,Zn-superoxide dismutase-linked ALS pathogenesis," *Proc. Natl. Acad. Sci. USA*, 2005, 102(30):10516-10521.
Roher et al., "β-Amyloid-(1-42) is a major component of cerebrovascular amyloid deposits: implications for the pathology of Alzheimer disease," *Proc. Natl. Acad. Sci. USA*, 1993, 90:10836-10840.
Ross and Poirier, "Protein aggregation and neurodegenerative disease," *Nature Med.*, 2004, S10-S17.
Roy et al., "Glutamate potentiates the toxicity of mutant Cu/Zn-superoxide dismutase in motor neurons by postsynaptic calcium-dependent mechanisms," *J. Neurosci.*, 1998, 18(23):9673-9684.
Ruangjirachuporn et al.,"Circulating immune complexes in serum from patients with dengue haemorrhagic fever," *Clin. Exp. Immunol.*, 1979 36:46-53.
Rubinstein et al., "Anti-platelet antibody interactions with Fc gamma receptor," *Semin. Thromb. Hemost.*, 1995, 21:10-22.
Sahu et al., "Binding kinetics, structure-activity relationship, and biotransformation of the complement inhibitor compstatin," *J. Immunol.*, 2000, 165:2491-2499.
Saphire et al., "A new look at rheumatoid factor," Cutting Edge Reports, from http://www.rheuma21st.com—pp. 1-9, 2001.
Saphire et al., "Crystal structure of a neutralizing human IgG against HIV-1: A template for vaccine design," *Science*, 2001, 293:1155-1159.

Sasso et al., "Antigenic specificities of human monoclonal and polyclonal IgM rheumatoid factors," *J. Immunol.*, 1988, 140(9):3098-3107.
Schenk and Yednock, "Immunization with amyloid-β attenuates Alzheimer's-disease-like pathology in the PDAPP mouse," *Nature*, 1999, 400:173-177.
Schenk and Yednock, "The role of microglia in Alzheimer's disease: friend or foe?" *Neurobiol. Aging*, 2002, 23:677-679.
Schlesinger and Chapman, "Influence of the human high-affinity IgG receptor FcgammaRI (CD64) on residual infectivity of neutralized dengue virus," *Virology*. vol. 260, No. 1 (Jul. 1999), pp. 84-88.
Shevtsova et al., "Promoters and serotypes: targeting of adeno-associated virus vectors for gene transfer in the rat central nervous system in vitro and in vivo," *Exp. Physiol.*, 2004, 90:53-59.
Shibata et al., "Presence of Cu/Zn SOD immunoreactivity in Neuronal Hyaline Inclusions in Spinal Cords from mice carrying a transgene for G93A Mutant Human SOD," *Acta Neuropathol.*, 1998, 95:136-142.
Shields et al., "High resolution mapping of the binding site on human IgG1 for FcγRI, FcγRII, FcγRIII, and FcRn and design of IgG1 variants with improved binding to the FcγR," *J. Biol. Chem.*, 2001, 276(9):6591-6604.
Sindic et al., "The binding of myelin basic protein to the Fc region of aggregated IgG and to immune complexes," *Clin. Exp. Immunol.*, 1980, 41:1-7.
Singh et al., "Reexamination of the mechanism of hydroxyl radical adducts formed from the reaction between familial amyotrophic lateral sclerosis-associated Cu,Zn superoxide dismutase mutants and H2O2," *Proc. Natl. Acad. Sci. USA*, 1998, 95:6675-6680.
Smith et al., "Autoimmunity and ALS," *Neurology*, 1996, (4 Suppl 2):S40-5; discussion S45-6. Review.
Smith et al., "Cytotoxicity of immunoglobulins from amyotrophic lateral sclerosis patients on a hybrid motoneuron cell line," *Proc. Natl. Acad. Sci. USA*, 1994, 91:3393-3397.
Sohi et al., "Crystallization of a complex between the Fab fragment of a human immunoglobulin M (IgM) rheumatoid factor (RF-AN) and the Fc fragment of human IgG4," *Immunol.*, 1996, 88:636-641.
Solomon, "Intravenous immunoglobulin and Alzheimer's disease immunotherapy," *Curr Opin. Mol. Therapeutics*, 9(1):79-85, 2007.
Sondermann et al., "Crystal structure of the soluble form of the human Fcγ-receptor IIb: a new member of the immunoglobulin superfamily at 1.7 Å resolution," *EMBO J.*, 1999, 18(5):1095-1103.
Sondermann et al., "The 3.2-Å crystal structure of the human IgG1 Fc fragment-FcγRIII complex," *Nature*, 2000, 406:267-273.
Song et al., "Fcγ receptor I- and III-Mediated macrophage inflammatory protein 1α induction in primary human and murine microglia," *Infect. Immun.*, 2002, 70(9):5177-5184.
Stasi and Provan, "Management of immune thrombocytopenic purpura in adults," *Mayo Clin Proc.* 79(4):504-522, 2004.
Steif et al, "Subunit interactions provide a significant contribution to the stability of the dimeric four-α—helical-bundle protein ROP," *Biochem.*, 1993,32:3867-3876.
Stieber et al., "Disruption of the structure of the Golgi apparatus and the function of the secretory pathway by mutants G93A and G85R of Cu, Zn superoxide dismutase (SOD1) of familial amyotrophic lateral sclerosis," *J. Neurol. Sci.*, 2004, 219:45-53.
Stone et al., "The Fc binding site for streptococcal protein G is in the Cγ2-Cγ3 interface region of IgG and is related to the sites that bind staphylococcal protein A and human rheumatoid factors," *J. Immunol.*, 1989, 143(2):565-570.
Sulica et al. "Effect of protein A of *Staphylococcus aureus* on the binding of monomeric and polymeric IgG to Fc receptor-bearing cells," *Immunology*, 1979, 38:173-179.
Takai, "Fc Receptors and their role in immune regulation and autoimmunity," 2005, *J Clin Immunology*, 2005, 25: 1-18.
Tamura et al., "The F(ab')2 fragment of an Aβ-specific monoclonal antibody reduces Aβ deposits in the brain," *Neurobiol. Disease*, 2005, 20:541-549.
Termaat et al., "Anti-DNA antibodies can bind to the glomerulus via two distinct mechanisms," *Kidney Int.*, 1992, 42:1363-1371.

(56) References Cited

OTHER PUBLICATIONS

Theodore et al., "Targeted overexpression of human 1-synuclein triggers microglial activation and adaptive immune response in a mouse model of Parkinson disease," *J. Neuropath. Exp. Neurol.*, 67(12):1149-1158, 2008.
Theofilopoulos et al., "The Raji Cell radioimmune assay for dectecting immune complexes in human sera," *J. Clin. Invest*, 1976, 57:169-182.
Tiwari and Hayward, "Familial amyotrophic lateral sclerosis mutants of copper/zinc superoxide dismutase are susceptible to disulfide reduction," *J. Biol. Chem.*, 2003, 278(8):5984-5992.
Tiwari et al., "Aberrantly increased hydrophobicity shared by mutants of Cu,Zn-superoxide dismutase in familial amyotrophic lateral sclerosis," *J. Biol. Chem.*, 2005, 280(33):29771-29779.
Trojanowski et al., "Altered Tau and neurofilament proteins in neurodegenerative diseases: diagnostic implications for Alzheimer's disease and Lewy body dementias," *Brain Pathology*, 1993, 3:45-54.
Tummala et al., "Inhibition of chaperone activity is a shared property of several Cu, Zn-SOD mutants that cause ALS," *J Biol Chem.*, 2005, 290:17725-17731.
Urushitani et al., "Chromogranin-mediated section of mutant SOD Proteins linked to ALS," *Nature Neuroscience*, 2006 9:108-118.
Valentine and Hart, "Misfolded CuZnSOD and amyotrophic lateral sclerosis," *Proc. Natl. Acad. Sci. USA*, 2003, 100(7):3617-3622.
Valentine et al., "Copper-zinc superoxide dismutase and amyotrophic lateral sclerosis," *Annu. Rev. Biochem.*, 2005, 74:563-593.
Vasileva and Jessberger, "Precise hit: adeno-associated virus in gene targeting," *Nature Microbiology Rev.*, 2005, 3:837-847.
Vaughn and Bjorkman, "Structural basis of pH-dependent antibody binding by the neonatal Fc receptor," *Structure*, 1998, 6:63-73.
Vedeler et al., "Fc receptors for immunoglobulin G—a role in the pathogenesis of Guillain-Barré syndrome and multiple sclerosis," *J. Neuroimmunol.*, 2001, 118:187-193.
Verdini and Viscomi, "Synthesis, resolution, and assignment of configuration of potent hypotensive retro-inverso bradykinin potentiation peptide 5a(BPPP$_{5a}$) analogues," *J. Chem. Soc. Perkin Trans.*, 1985, I:697-701.
Verkhivker et al., "Monte Carlo simulations of the peptide recognition at the consensus binding site of the constant fragment of human immunoglobulin G: the energy landscape analysis of a hot spot at the intermolecular interface," *Proteins*, 2002, 48(3):539-557.
Walker et al., "Using protein-based motifs to stabilize peptides," *J Peptide Res.*, 2003; 62:214-226.
Wallace et al., "Role of Fcγ receptors in cancer and infectious disease," *J. Leukocyte Biol.*, 1994, 55:816-826.
Wang et al., "Copper-binding-site-null SOD1 causes ALS in transgenic mice: aggregates of non-native SOD1 delineate a feature" *Human Molecular Genetics*, 2003, vol. 12, No. 21 2753-2764.
Webster et al., "Antibody-Mediated phagocytosis of the amyloid b-peptide in micoglia is differentially modulated by C1q," *J Immunol.*, 2001, 166:7496-7503.
West, Jr. and Bjorkman, "Crystal structure and immunoglobulin G binding properties of the human major histocompatibility complex-related Fc receptor," *Biochemistry*, 2000, 39:9698-9708.
Wines et al., "The IgG Fc contains distinct Fc receptor (FcR) binding sites: the leukocyte receptors FcγRI and FcγRIIa bind to a region in the Fc distinct from that recognized by neonatal FcR and protein A," *J. Immunol.*, 2000, 164: 5313-5318.
Wines et al., "Soluble FcgammaRIIa inhibits rheumatoid factor binding to immune complexes," *Immunol.*, 2003, 109:246-254.
Witz and Ran, "FcR may function as a progression factor of nonlymphoid tumors," *Immunol. Res.*, 1992, 11:283-295.
Yim et al., "A familial amyotrophic lateral sclerosis-associated A4V Cu, Zn-superoxide dismutase mutant has a lower Km for hydrogen peroxide. Correlation between clinical severity and the Km value," *J. Biol. Chem.*, 1997, 272:8861-8863.
Yim et al., "A gain-of-function of an amyotrophic lateral sclerosis-associated Cu,Zn-superoxide dismutase mutant: An enhancement of free radical formation due to a decrease in Km for hydrogen peroxide," *Proc. Natl. Acad. Sci. USA*, 1996, 93:5709-5714.
Yim et al., "Copper, zinc superoxide dismutase catalyzes hydroxyl radical production from hydrogen peroxide," *Proc. Natl. Acad. Sci. USA*, 1990, 87:5006-5010.
Yim et al., "Enzyme Function of Copper, zinc superoxide dismutase as a free radical generator," *J. Biol. Chem.*, 1993, 268(6):4099-4105.
Zack et al., "Localization of an Fc-binding reactivity to the constant region of human IgG4," *J. Immunol.*, 1995, 155:5057-5063.
Zhang et al, "Bicarbonate Enhances Peroxidase Activity of Cu,Zn-Superoxide Dismutase," *J Biol Chem.*, 2002, 277:1013-1020.
Zhang et al., "Conformational changes of the flavivirus E glycoprotein," *Structure*, 2004 12:1607-1618.
Zhang et al., "Bicarbonate Enhances the Hydroxylation, Nitration, and Peroxidation Reactions Catalyzed by Copper, Zinc Superoxide Dismutase," *J. Biol. Chem.*, 2000, 275:14038-14045.
Zhao et al., "Activated microglia initiate motor neuron injury by a nitric oxide and glutamate-mediated mechanism," *J. Neuropathol. Exp. Neurol.*, 2004, 63(9):964-977.
International Search Report and Written Opinion for PCT/US2009/050966, mailed Feb. 22, 2010, 7 pages.
International Preliminary Report on Patentability for PCT/US2009/050966, issued Jan. 18, 2011, 5 pages.
European Search Report for European Application No. 09798797.8, dated Jun. 22, 2012, 6 pages.
Search Report and Written Opinion by the Hungarian Intellectual Property Office for Singapore Application No. 201100335-7, mailed Feb. 1, 2013, 12 pages.
Rodrigo et al., "Differential enhancement of dengue virus immune complex infectivity mediated by signaling-competent and signaling-incompetent human Fcgamma RIA (CD64) or FcgammaRIIA (CD32)," J. Virol., 80(20):10128-10138, Oct. 2006.
Written Opinion for Singapore App. No. 201100335-7, mailed Nov 28, 2013, 9 pages.

\* cited by examiner

SEQUENCE LISTING

```
<160> NUMBER OF SEQ ID NOS: 56

<210> SEQ ID NO 1
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=absent any amino acid
<220> FEATURE:
<221> NAME/KEY: VARIANT
<222> LOCATION: 4
<223> OTHER INFORMATION: Xaa=Phe, Tyr, Trp, 5-Hydoxytryptophan (5-HTP),
      or Arg
<220> FEATURE:
<221> NAME/KEY: VARIANT
<222> LOCATION: 6
<223> OTHER INFORMATION: Xaa=any amino acid
<220> FEATURE:
<221> NAME/KEY: VARIANT
<222> LOCATION: 7
<223> OTHER INFORMATION: Xaa=Gly or Ala
<220> FEATURE:
<221> NAME/KEY: VARIANT
<222> LOCATION: 8
<223> OTHER INFORMATION: Xaa=Glu or Ala
<220> FEATURE:
<221> NAME/KEY: VARIANT
<222> LOCATION: 13
<223> OTHER INFORMATION: Xaa=absent or any amino acid

<400> SEQUENCE: 1

Xaa Cys Ala Xaa His Xaa Xaa Xaa Leu Val Trp Cys Xaa
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Synthetic

<400> SEQUENCE: 2

Asp Cys Ala Trp His Leu Gly Glu Leu Val Trp Cys Thr
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Asp Cys Ala Phe His Leu Gly Glu Leu Val Trp Cys Thr
 1               5                  10

<210> SEQ ID NO 4
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 4

Asp Cys Ala Arg His Leu Gly Glu Leu Val Trp Cys Thr
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Arg Cys Ala Arg His Leu Gly Glu Leu Val Trp Cys Thr
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Arg Cys Ala Trp His Leu Gly Glu Leu Val Trp Cys Thr
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Synthetic

<400> SEQUENCE: 7

Arg Cys Ala Phe His Leu Gly Glu Leu Val Trp Cys Thr
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 3
<223> OTHER INFORMATION: Xaa=Phe, Tyr, Trp, or Arg

<400> SEQUENCE: 8

Cys Ala Xaa His Leu Gly Glu Leu Val Trp Cys
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Cys Ala Phe His Leu Gly Glu Leu Val Trp Cys Thr
 1               5                  10
```

```
<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Cys Ala Trp His Leu Gly Glu Leu Val Trp Cys Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Cys Ala Arg His Leu Gly Glu Leu Val Trp Cys Thr
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid
<220> FEATURE:
<221> NAME/KEY: VARIANT
<222> LOCATION: 6
<223> OTHER INFORMATION: Xaa=Trp, Tyr, Phe, or Arg

<400> SEQUENCE: 12

Xaa Pro Pro Cys Ala Xaa His Leu Gly Glu Leu Val Trp Cys Thr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 13

Xaa Pro Pro Cys Ala Trp His Leu Gly Glu Leu Val Trp Cys Thr
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Ala Pro Pro Cys Ala Trp His Leu Gly Glu Leu Val Trp Cys Thr
1               5                   10                  15
```

```
<210> SEQ ID NO 15
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 15

Xaa Pro Pro Cys Ala Arg His Leu Gly Glu Leu Val Trp Cys Thr
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Ala Pro Pro Cys Ala Arg His Leu Gly Glu Leu Val Trp Cys Thr
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 17

Xaa Pro Pro Cys Ala Phe His Leu Gly Glu Leu Val Trp Cys Thr
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Ala Pro Pro Cys Ala Phe His Leu Gly Glu Leu Val Trp Cys Thr
 1               5                  10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 19

Xaa Pro Pro Asp Cys Ala Trp His Leu Gly Glu Leu Val Trp Cys Thr
 1               5                  10                  15

<210> SEQ ID NO 20
<211> LENGTH: 16
```

```
<212> TYPE: PRT
<213> ORGANISM: Artificial Sequence
<220> FEATURE:
<223> OTHER INFORMATION: Synthetic

<400> SEQUENCE: 20

Ala Pro Pro Asp Cys Ala Trp His Leu Gly Glu Leu Val Trp Cys Thr
 1               5                  10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 21

Xaa Pro Pro Asp Cys Ala Arg His Leu Gly Glu Leu Val Trp Cys Thr
 1               5                  10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic

<400> SEQUENCE: 22

Ala Pro Pro Asp Cys Ala Arg His Leu Gly Glu Leu Val Trp Cys Thr
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 23

Xaa Pro Pro Asp Cys Ala Phe His Leu Gly Glu Leu Val Trp Cys Thr
 1               5                  10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

Ala Pro Pro Asp Cys Ala Phe His Leu Gly Glu Leu Val Trp Cys Thr
 1               5                  10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
```

```
<222> LOCATION: 1
<223> OTHER INFORMATION: Xaa=any amino acid

<400> SEQUENCE: 25

Xaa Pro Pro Arg Cys Ala Trp His Leu Gly Glu Leu Val Trp Cys Thr
 1               5                  10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic

<400> SEQUENCE: 26

Ala Pro Pro Arg Cys Ala Trp His Leu Gly Glu Leu Val Trp Cys Thr
 1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 27

Xaa Pro Pro Arg Cys Ala Arg His Leu Gly Glu Leu Val Trp Cys Thr
 1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic

<400> SEQUENCE: 28

Ala Pro Pro Arg Cys Ala Arg His Leu Gly Glu Leu Val Trp Cys Thr
 1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa=any amino acid

<400> SEQUENCE: 29

Xaa Pro Pro Arg Cys Ala Phe His Leu Gly Glu Leu Val Trp Cys Thr
 1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic

<400> SEQUENCE: 30

Ala Pro Pro Arg Cys Ala Phe His Leu Gly Glu Leu Val Trp Cys Thr
```

```
1               5                   10                  15
```

<210> SEQ ID NO 31
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 15
<223> OTHER INFORMATION: Xaa=any amino acid

<400> SEQUENCE: 31

```
Cys Ala Trp His Leu Gly Glu Leu Val Trp Cys Thr Pro Pro Xaa
 1               5                   10                  15
```

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

```
Cys Ala Trp His Leu Gly Glu Leu Val Trp Cys Thr Pro Pro Ala
 1               5                   10                  15
```

<210> SEQ ID NO 33
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 15
<223> OTHER INFORMATION: Xaa=any amino acid

<400> SEQUENCE: 33

```
Cys Ala Arg His Leu Gly Glu Leu Val Trp Cys Thr Pro Pro Xaa
 1               5                   10                  15
```

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

```
Cys Ala Arg His Leu Gly Glu Leu Val Trp Cys Thr Pro Pro Ala
 1               5                   10                  15
```

<210> SEQ ID NO 35
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 15
<223> OTHER INFORMATION: Xaa=any amino acid

<400> SEQUENCE: 35

```
Cys Ala Phe His Leu Gly Glu Leu Val Trp Cys Thr Pro Pro Xaa
 1               5                   10                  15
```

```
<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Cys Ala Phe His Leu Gly Glu Leu Val Trp Cys Thr Pro Pro Ala
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 16
<223> OTHER INFORMATION: Xaa=any amino acid

<400> SEQUENCE: 37

Asp Cys Ala Trp His Leu Gly Glu Leu Val Trp Cys Thr Pro Pro Xaa
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic

<400> SEQUENCE: 38

Asp Cys Ala Trp His Leu Gly Glu Leu Val Trp Cys Thr Pro Pro Ala
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 16
<223> OTHER INFORMATION: Xaa=any amino acid

<400> SEQUENCE: 39

Asp Cys Ala Arg His Leu Gly Glu Leu Val Trp Cys Thr Pro Pro Xaa
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Asp Cys Ala Arg His Leu Gly Glu Leu Val Trp Cys Thr Pro Pro Ala
1               5                   10                  15

<210> SEQ ID NO 41
<211> LENGTH: 16
<212> TYPE: PRT
<213> ORGANISM: Artificial Sequence
<220> FEATURE:
```

```
<223> OTHER INFORMATION: Synthetic
<220> FEATURE:
<221> NAME/KEY: VARIANT
<222> LOCATION: 16
<223> OTHER INFORMATION: Xaa=any amino acid

<400> SEQUENCE: 41

Asp Cys Ala Phe His Leu Gly Glu Leu Val Trp Cys Thr Pro Pro Xaa
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Asp Cys Ala Phe His Leu Gly Glu Leu Val Trp Cys Thr Pro Pro Ala
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 16
<223> OTHER INFORMATION: Xaa=any amino acid

<400> SEQUENCE: 43

Arg Cys Ala Trp His Leu Gly Glu Leu Val Trp Cys Thr Pro Pro Xaa
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic

<400> SEQUENCE: 44

Arg Cys Ala Trp His Leu Gly Glu Leu Val Trp Cys Thr Pro Pro Ala
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 16
<223> OTHER INFORMATION: Xaa=any amino acid

<400> SEQUENCE: 45

Arg Cys Ala Arg His Leu Gly Glu Leu Val Trp Cys Thr Pro Pro Xaa
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic
```

```
<400> SEQUENCE: 46

Arg Cys Ala Arg His Leu Gly Glu Leu Val Trp Cys Thr Pro Pro Ala
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 16
<223> OTHER INFORMATION: Xaa=any amino acid

<400> SEQUENCE: 47

Arg Cys Ala Phe His Leu Gly Glu Leu Val Trp Cys Thr Pro Pro Xaa
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic

<400> SEQUENCE: 48

Arg Cys Ala Phe His Leu Gly Glu Leu Val Trp Cys Thr Pro Pro Ala
1               5                   10                  15

<210> SEQ ID NO 49
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 4
<223> OTHER INFORMATION: Xaa=absent or any amino acid
<220> FEATURE:
<221> NAME/KEY: VARIANT
<222> LOCATION: 7
<223> OTHER INFORMATION: Xaa=Phe, Tyr, 5-HTP, Trp, or Arg
<220> FEATURE:
<221> NAME/KEY: VARIANT
<222> LOCATION: 9
<223> OTHER INFORMATION: Xaa=any amino acid
<220> FEATURE:
<221> NAME/KEY: VARIANT
<222> LOCATION: 10
<223> OTHER INFORMATION: Xaa=Gly or Ala
<220> FEATURE:
<221> NAME/KEY: VARIANT
<222> LOCATION: 11
<223> OTHER INFORMATION: Xaa=Glu or Ala
<220> FEATURE:
<221> NAME/KEY: VARIANT
<222> LOCATION: 16
<223> OTHER INFORMATION: Xaa=absent or any amino ac

<400> SEQUENCE: 49

Trp Glu Ala Xaa Cys Ala Xaa His Xaa Xaa Xaa Leu Val Trp Cys Xaa
1               5                   10                  15

Lys Val Glu Glu
            20

<210> SEQ ID NO 50
<211> LENGTH: 20
<212> TYPE: PRT
```

```
<213> ORGANISM: Artificial Sequence
<220> FEATURE:
<223> OTHER INFORMATION: Synthetic
<220> FEATURE:
<221> NAME/KEY: VARIANT
<222> LOCATION: 7
<223> OTHER INFORMATION: Xaa=Arg, Trp, 5-HTP, Tyr, or Phe

<400> SEQUENCE: 50

Trp Glu Ala Asp Cys Ala Xaa His Leu Gly Glu Leu Val Trp Cys Thr
 1               5                  10                  15

Lys Val Glu Glu
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic

<400> SEQUENCE: 51

Trp Glu Ala Asp Cys Ala Trp His Leu Gly Glu Leu Val Trp Cys Thr
 1               5                  10                  15

Lys Val Glu Glu
            20

<210> SEQ ID NO 52
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1,2,3,4,5,6,18,19,20,21,22
<223> OTHER INFORMATION: Xaa=absent or any amino acid
<220> FEATURE:
<221> NAME/KEY: VARIANT
<222> LOCATION: 9
<223> OTHER INFORMATION: Xaa=Phe, Tyr, 5-HTP, Trp, or Arg
<220> FEATURE:
<221> NAME/KEY: VARIANT
<222> LOCATION: 11
<223> OTHER INFORMATION: Xaa=any amino acid
<220> FEATURE:
<221> NAME/KEY: VARIANT
<222> LOCATION: 12
<223> OTHER INFORMATION: Xaa=Gly or Ala
<220> FEATURE:
<221> NAME/KEY: VARIANT
<222> LOCATION: 13
<223> OTHER INFORMATION: Xaa=Glu or Ala

<400> SEQUENCE: 52

Xaa Xaa Xaa Xaa Xaa Xaa Cys Ala Xaa His Xaa Xaa Xaa Leu Val Trp
 1               5                  10                  15

Cys Xaa Xaa Xaa Xaa Xaa
            20

<210> SEQ ID NO 53
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1,2,3,4,5,18,19,20,21,22
<223> OTHER INFORMATION: Xaa=absent or any amino acid
```

-continued

```
<220> FEATURE:
<221> NAME/KEY: VARIANT
<222> LOCATION: 8
<223> OTHER INFORMATION: Xaa=Trp, Tyr, Phe, 5-Hydroxytrphophan (5-HTP),
      5-hydroxytryptamine (5-HT), or another amino acid
      derivative

<400> SEQUENCE: 53

Xaa Xaa Xaa Xaa Xaa Cys Ala Xaa His Leu Gly Glu Leu Val Trp Cys
 1               5                  10                  15

Thr Xaa Xaa Xaa Xaa Xaa
            20

<210> SEQ ID NO 54
<211> LENGTH: 22
<212> TYPE: PRT
<213> ORGANISM: Artificial Sequence
<220> FEATURE:
<223> OTHER INFORMATION: Synthetic

<400> SEQUENCE: 54

Ala Ala Ala Ala Ala Asp Cys Ala Arg His Leu Gly Glu Leu Val Trp
 1               5                  10                  15

Cys Ala Ala Ala Ala Ala
            20

<210> SEQ ID NO 55
<211> LENGTH: 17
<212> TYPE: PRT
<213> ORGANISM: Artificial Sequence
<220> FEATURE:
<223> OTHER INFORMATION: Synthetic

<400> SEQUENCE: 55

Ala Ala Arg Cys Ala Arg His Leu Gly Glu Leu Val Trp Cys Thr Ala
 1               5                  10                  15

Ala

<210> SEQ ID NO 56
<211> LENGTH: 19
<212> TYPE: PRT
<213> ORGANISM: Artificial Sequence
<220> FEATURE:
<223> OTHER INFORMATION: Synthetic

<400> SEQUENCE: 56

Ala Ala Ala Asp Cys Ala Phe Trp His Leu Gly Glu Leu Val Trp Cys
 1               5                  10                  15

Thr Ala Ala
```

METHODS FOR TREATING IMMUNE-MEDIATED DENGUE FEVER INFECTIONS AND ANTIBODY-DEPENDENT ENHANCEMENT OF DENGUE FEVER INFECTIONS, INCLUDING DENGUE HEMORRHAGIC FEVER AND DENGUE SHOCK SYNDROME

CROSS-REFERENCE TO RELATED APPLICATION

This application is a National Stage application under 35 U.S.C. 371 and claims benefit under 35 U.S.C. 119(a) of International Application No. PCT/US2009/050966 having an International Filing Date of Jul. 17, 2009, which claims benefit of priority from U.S. Provisional Application Ser. No. 61/081,943, filed on Jul. 18, 2008.

TECHNICAL FIELD

This document relates to inhibition of immune complex formation associated with viral infection. For example, this document provides materials and methods for inhibiting immune complex formation in Dengue Fever (DF) infections and antibody-dependent-enhancement (ADE) of DF infections, including Dengue Hemorrhagic Fever (DHF) and Dengue Shock Syndrome (DSS). In particular, this document relates to inhibition of immune complex formation by polypeptides and other small molecules.

BACKGROUND

Humoral immune responses are triggered when an antigen binds specifically to an antibody. The combination of an antibody molecule and an antigen forms a small, relatively soluble immune complex. Antigens either can be foreign substances, such as viral or bacterial polypeptides, or can be "self-antigens" such as polypeptides normally found in the human body. The immune system normally distinguishes foreign antigens from self-antigens. "Autoimmune" disease can occur, however, when this system breaks down, such that the immune system turns upon the body and destroys tissues or organ systems as if they were foreign substances. Larger immune complexes are more pathogenic than small, more soluble immune complexes. The formation of large, relatively insoluble immune complexes can result from both the interaction of antibody molecules with antigen and the interaction of antibody molecules with each other. Such immune complexes also can result from interactions between antibodies in the absence of antigen.

Antibodies can prevent infections by coating viruses or bacteria, but otherwise are relatively harmless by themselves. In contrast, organ specific tissue damage can occur when antibodies combine with antigens and the resulting immune complexes bind to certain effector molecules in the body. Effector molecules are so named because they carry out the pathogenic effects of immune complexes. By inhibiting the formation of large, insoluble immune complexes, or by inhibiting the binding of immune complexes to effector molecules, the tissue damaging effects of immune complexes may be prevented.

SUMMARY

This document is based in part on the discovery that polypeptides having amino acid sequences based on those set forth in SEQ ID NO:2 and SEQ ID NO:20 (also referred to herein as NB-406) can bind specifically and with high affinity to the $C_H2$-$C_H3$ domain of immunoglobulin molecules, thus inhibiting the formation of insoluble immune complexes containing antibodies and antigens, and preventing the binding of such complexes to effector molecules. This document provides such polypeptides, other $C_H2$-$C_H3$ binding compounds, compostions containing the polypeptides and/or compounds, and methods for using the polypeptides and compositions to inhibit immune complex formation and therapeutic use in treating viral infections.

In one aspect, this document features a method for inhibiting immune complex formation in a subject, the method comprising administering to the subject a composition comprising a purified polypeptide, the polypeptide comprising the amino acid sequence $(Xaa_1)_m$-Cys-Ala-$Xaa_2$-His-Leu-Gly-Glu-Leu-Val-Trp-Cys-Thr-$(Xaa_3)_n$ (SEQ ID NO:53), wherein $Xaa_1$ is any amino acid, $Xaa_2$ is Trp, Tyr or Phe, 5-Hydroxytrphophan (5-HTP), 5-hydroxytryptamine (5-HT), or another amino acid derivative, $Xaa_3$ is any amino acid, and m and n independently are 0, 1, 2, 3, 4, or 5, and wherein the immune complex formation is associated with a viral infection. The immune complex formation can be associated with Antibody Dependent Enchancement (ADE) of Dengue Fever or infection by Dengue Virus (DENV), or contributes to the enhacement of a DENV infection. The peptide can cause clinical or histological improvement of a DENV infection. The peptide can cause an improvement in or delay the onset of one or more of the histiological characteristics of a DENV infection. The peptide can decrease the ADE of a DENV infection.

The DENV infection can be Dengue Hemorragic Fever (DHF) or Dengue Shock Syndrome (DSS). The peptide can inhibit binding of an anti-DENV heterologous IgG immune complex (IC) to an FcγR. The peptide can inhibit formation of IC that contribute to immunopathogenesis of the ADE of DENV infections. The peptide can inhibit binding of DENV virons to IgG IC. The peptide can inhibit binding of a DENV protein (e.g., NS1) to an IgG immune complex. The peptide can inhibit binding of TNF-α to IgG IC. The peptide can inhibit binding of a DENV-IgG IC to FcγI, FcγIIa H131 allele, FcγIIa R131 allele, FcγRIIb, FcγRIIc, FcγRIIIa, or FcγγIIIb. The peptide can inhibit binding of DENV-IgG IC to mC1q or sC1q.

The polypeptide can comprise a terminal stabilizing group. The terminal stabilizing group can be at the amino terminus of the polypeptide and can be a tripeptide having the amino acid sequence Xaa-Pro-Pro, wherein Xaa is any amino acid (e.g., Ala). The terminal stabilizing group can be at the carboxy terminus of the polypeptide and can be a tripeptide having the amino acid sequence Pro-Pro-Xaa, wherein Xaa is any amino acid (e.g., Ala).

The method can further comprise the step of monitoring the subject for one or more clinical, histiopatholigical or molecular characteristics of hemorrhagic fever. The one or more clinical, histiopathological, or molecular characteristics of hemorrhagic fever can be selected from the group consisting of a decrease in platelets, hemoconcentration, or an increase in FcγR+ effector cells.

The polypeptide can comprise the amino acid sequence Xaa-Pro-Pro-Asp-Cys-Ala-Trp-His-Leu-Gly-Glu-Leu-Val-Trp-Cys-Thr (SEQ ID NO:19), wherein Xaa is any amino acid. The polypeptide can comprise the amino acid sequence Ala-Pro-Pro-Asp-Cys-Ala-Trp-His-Leu-Gly-Glu-Leu-Val-Trp-Cys-Thr (SEQ ID NO:20). The polypeptide can comprise the amino acid sequence Asp-Cys-Ala-Trp-His-Leu-Gly-Glu-Leu-Val-Trp-Cys-Thr (SEQ ID NO:2).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and from the claims.

DETAILED DESCRIPTION

This document provides polypeptides and other compounds capable of interacting with the $C_H2$-$C_H3$ cleft of an immunoglobulin molecule, such that interaction of the immunoglobulin with other molecules (e.g., effectors or other immunoglobulins) is blocked. Methods for identifying such polypeptides and other compounds also are described, along with compositions and articles of manufacture containing the polypeptides and compounds. In addition, this document provides methods for using the polypeptides and compounds to inhibit immune complex formation and to treat diseases (e.g., viral diseases such as Dengue Fever) in which IgG immune complexes bind to effector molecules, such as membrane bound C1q (mC1q), soluble C1q (sC1q), and FcγR5 (including, but not limited to FcγRI (and isoforms of FcγRs), FcγRIIa, FcγRIIb/c, FcγRIIIa, FcγRIIIb, and FcRn).

Immunoglobulins

The immunoglobulins make up a class of proteins found in plasma and other bodily fluids that exhibit antibody activity and bind to other molecules (e.g., antigens and certain cell surface receptors) with a high degree of specificity. Based on their structure and biological activity, immunoglobulins can be divided into five classes: IgM, IgG, IgA, IgD, and IgE. IgG is the most abundant antibody class in the body; this molecule assumes a twisted "Y" shape configuration. With the exception of the IgMs, immunoglobulins are composed mainly of four peptide chains that are linked by several intrachain and interchain disulfide bonds. For example, the IgGs are composed of two polypeptide heavy chains (H chains) and two polypeptide light chains (L chains), which are coupled by disulfide bonds and non-covalent bonds to form a protein molecule with a molecular weight of approximately 150,000 daltons (Saphire et al., "Crystal Structure of a Neutralizing Human IgG Against HIV-1: A Template for Vaccine Design," *Science,* 2001, 293:1155-1159). The average IgG molecule contains approximately 4.5 interchain disulfide bonds and approximately 12 intrachain disulfide bonds (Frangione and Milstein (1968) *J. Mol. Biol.* 33:893-906).

The light and heavy chains of immunoglobulin molecules are composed of constant regions and variable regions (see, e.g., Padlan (1994) *Mol. Immunol.* 31:169-217). For example, the light chains of an IgG1 molecule each contain a variable domain ($V_L$) and a constant domain ($C_L$). The heavy chains each have four domains: an amino terminal variable domain ($V_H$), followed by three constant domains ($C_H1$, $C_H2$, and the carboxy terminal $C_H3$). A hinge region corresponds to a flexible junction between the $C_H1$ and $C_H2$ domains. Papain digestion of an intact IgG molecule results in proteolytic cleavage at the hinge and produces an Fc fragment that contains the $C_H2$ and $C_H3$ domains, and two identical Fab fragments that each contain a $C_H1$, $C_L$, $V_H$, and $V_L$ domain. The Fc fragment has complement- and tissue-binding activity, while the Fab fragments have antigen-binding activity.

Immunoglobulin molecules can interact with other polypeptides through various regions. The majority of antigen binding, for example, occurs through the $V_L/V_H$ region of the Fab fragment. The hinge region also is thought to be important, as immunological dogma states that the binding sites for Fc receptors (FcR) are found in the hinge region of IgG molecules (see, e.g., Raghavan and Bjorkman (1996) *Annu. Rev. Dev. Biol.* 12:181-200). More recent evidence, however, suggests that FcR interacts with the hinge region primarily when the immunoglobulin is monomeric (i.e., not immune-complexed). Such interactions typically involve the amino acids at positions 234-237 of the Ig molecule (Wiens et al. (2000) *J. Immunol.* 164:5313-5318).

Immunoglobulin molecules also can interact with other polypeptides through a cleft within the $C_H2$-$C_H3$ domain. The "$C_H2$-$C_H3$ cleft" typically includes the amino acids at positions 251-255 within the $C_H2$ domain and the amino acids at positions 424-436 within the $C_H3$ domain. As used herein, numbering is with respect to an intact IgG molecule as in Kabat et al. (*Sequences of Proteins of Immunological Interest,* $5^{th}$ ed., Public Health Service, U.S. Department of Health and Human Services, Bethesda, Md.). The corresponding amino acids in other immunoglobulin classes can be readily determined by those of ordinary skill in the art.

The $C_H2$-$C_H3$ cleft is unusual in that it is characterized by both a high degree of solvent accessibility and a predominantly hydrophobic character, suggesting that burial of an exposed hydrophobic surface is an important driving force behind binding at this site. A three-dimensional change occurs at the IgG $C_H2$-$C_H3$ cleft upon antigen binding, allowing certain residues (e.g., a histidine at position 435) to become exposed and available for binding. Direct evidence of three-dimensional structural changes that occur upon antigen binding was found in a study using monoclonal antibodies sensitive to conformational changes in the Fc region of human IgG. Five IgG epitopes were altered by antigen binding: two within the hinge region and three within the $C_H2$-$C_H3$ cleft (Girkontraite et al. (1996) *Cancer Biother. Radiopharm.* 11:87-96). Antigen binding therefore can be important for determining whether an immunoglobulin binds to other molecules through the hinge or the Fc $C_H2$-$C_H3$ region.

The Fc region can bind to a number of effector molecules and other proteins, including the following:

(1) FcRn—The neonatal Fc receptor determines the half life of the antibody molecule in the general circulation (Leach et al., (1996) *J. Immunol.* 157:3317-3322; Gheti and Ward (2000) *Ann. Rev. Immunol.* 18:739-766). Mice genetically lacking FcRn are protected from the deleterious effects of pathogenic autoantibodies due to the shortened half-life of the autoantibodies (Liu et al. (1997) *J. Exp. Med.* 186:777-783). The only binding site of FcRn to the IgG Fc is the IgG Fc $C_H2$-$C_H3$ cleft and HIS 435 has been shown by 3D structure and alanine scan to be essential to FcRn to IgG Fc binding (Shields et al. (2001) *J. Biol. Chem.* 276:6591-6604 and Martin et al. (2001) *Mol. Cell,* 7:867-877). Since the peptides described herein bind with high affinity to the $C_H2$-$C_H3$ cleft and HIS 435, the peptides are direct inhibitors of (immune complexed) IgG Fc to FcRn binding. An inhibitor of FcRn binding to immune complexes or to pathogenic autoantibodies would be useful in treating diseases involving pathogenic autoantibodies and/or immune complexes.

(2) FcR—The cellular Fc Receptor provides a link between the humoral immune response and cell-mediated effector systems (Hamano et al. (2000) *J. Immunol.* 164: 6113-6119; Coxon et al. (2001) *Immunity* 14:693-704; Fossati et al. (2001) *Eur. J. Clin. Invest.* 31:821-831). The Fcγ Receptors are specific for IgG molecules, and include FcγRI, FcγRIIa, FcγRIIb/c, and FcγRIIIa/b (and alleles, phenotypes and genotypes thereof). These isotypes bind with differing affinities to monomeric and immune-complexed IgG.

(3) C1q—The first component of the classical complement pathway is C1, which exists in blood serum as a complex of three proteins, C1q, C1r, and C1s. The classical complement pathway is activated when C1q binds to the Fc regions of antigen-bound IgG or IgM. Although the binding of C1q to a single Fc region is weak, C1q can form tight bonds to a cluster of Fc regions. At this point C1 becomes proteolytically active.

The formation of immune complexes via interactions between immunoglobulin Fc regions and other antibodies or other factors (e.g., those described above) is referred to herein as "Fc-mediated immune complex formation" or "the Fc-mediated formation of an immune complex." Immune complexes containing such interactions are termed "Fc-mediated immune complexes." Fc-mediated immune complexes can include immunoglobulin molecules with or without bound antigen, and typically include $C_H2$-$C_H3$ cleft-specific ligands that have higher binding affinity for immune complexed antibodies than for monomeric antibodies.

Purified Polypeptides

As used herein, a "polypeptide" is any chain of amino acid residues, regardless of post-translational modification (e.g., phosphorylation or glycosylation). The polypeptides provided herein typically are between 10 and 50 amino acids in length (e.g., 10, 11, 12, 13, 14, 15, 20, 25, 30, 35, 40, 45, or 50 amino acids in length). Polypeptides that are between 10 and 20 amino acids in length (e.g., 10, 11, 12, 13, 14, 15, 16, 17, 18, 19, or 20 amino acids in length) can be particularly useful.

The amino acid sequences of the polypeptides provided herein are somewhat constrained, but can have some variability. For example, the polypeptides provided herein typically include the amino acid sequence $Xaa_1$-Cys-Ala-$Xaa_2$-His-$Xaa_3$-$Xaa_4$-$Xaa_5$-Leu-Val-Trp-Cys-$Xaa_6$ (SEQ ID NO:1), wherein the residues denoted by $Xaa_n$ can display variability. For example, $Xaa_1$ can be absent or can be any amino acid (e.g., Arg or Asp). $Xaa_2$ can be Phe, Tyr, Trp, 5-Hydroxytryptophan (5-HTP), or Arg. $Xaa_3$ can be any amino acid. $Xaa_4$ can be Gly or Ala, while $Xaa_5$ can be Glu or Ala. Like $Xaa_1$, $Xaa_6$ also can be absent or can be any amino acid.

In one embodiment, a polypeptide can include the amino acid sequence Asp-Cys-Ala-Trp-His-Leu-Gly-Glu-Leu-Val-Trp-Cys-Thr (SEQ ID NO:2). Alternatively, a polypeptide can include the amino acid sequence Asp-Cys-Ala-Phe-His-Leu-Gly-Glu-Leu-Val-Trp-Cys-Thr (SEQ ID NO:3) or Asp-Cys-Ala-Arg-His-Leu-Gly-Glu-Leu-Val-Trp-Cys-Thr (SEQ ID NO:4). In another embodiment, a polypeptide can include the amino acid sequence Arg-Cys-Ala-Arg-His-Leu-Gly-Glu-Leu-Val-Trp-Cys-Thr (SEQ ID NO: 5), Arg-Cys-Ala-Trp-His-Leu-Gly-Glu-Leu-Val-Trp-Cys-Thr (SEQ ID NO: 6), or Arg-Cys-Ala-Phe-His-Leu-Gly-Glu-Leu-Val-Trp-Cys-Thr (SEQ ID NO:7).

In another embodiment, a polypeptide can include the amino acid sequence Cys-Ala-Xaa-His-Leu-Gly-Glu-Leu-Val-Trp-Cys (SEQ ID NO:8), in which Xaa can be Phe, Tyr, Trp, or Arg. For example, this document provides polypeptides that include the following amino acid sequences: Cys-Ala-Phe-His-Leu-Gly-Glu-Leu-Val-Trp-Cys-Thr (SEQ ID NO:9), Cys-Ala-Trp-His-Leu-Gly-Glu-Leu-Val-Trp-Cys-Thr (SEQ ID NO:10), and Cys-Ala-Arg-His-Leu-Gly-Glu-Leu-Val-Trp-Cys-Thr (SEQ ID NO:11).

The polypeptides provided herein can be modified for use in vivo by the addition, at the amino- or carboxy-terminal end, of a stabilizing agent to facilitate survival of the polypeptide in vivo. This can be useful in situations in which peptide termini tend to be degraded by proteases prior to cellular uptake. Such blocking agents can include, without limitation, additional related or unrelated peptide sequences that can be attached to the amino- and/or carboxy-terminal residues of the polypeptide (e.g., an acetyl group attached to the N-terminal amino acid or an amide group attached to the C-terminal amino acid). Such attachment can be achieved either chemically, during the synthesis of the polypeptide, or by recombinant DNA technology using methods familiar to those of ordinary skill in the art. Alternatively, blocking agents such as pyroglutamic acid or other molecules known in the art can be attached to the amino- and/or carboxy-terminal residues, or the amino group at the amino terminus or the carboxy group at the carboxy terminus can be replaced with a different moiety.

A proline or an Xaa-Pro-Pro (e.g., Ala-Pro-Pro) sequence at the amino terminus can be particularly useful (see, e.g., WO 00/22112). For example, a polypeptide can include the amino acid sequence $Xaa_1$-Pro-Pro-Cys-Ala-$Xaa_2$-His-Leu-Gly-Glu-Leu-Val-Trp-Cys-Thr (SEQ ID NO:12), where $Xaa_1$ is any amino acid (e.g., Ala), and $Xaa_2$ is Trp, Tyr, Phe, or Arg. For example, a polypeptide can include the amino acid sequence Xaa-Pro-Pro-Cys-Ala-Trp-His-Leu-Gly-Glu-Leu-Val-Trp-Cys-Thr (SEQ ID NO:13), Ala-Pro-Pro-Cys-Ala-Trp-His-Leu-Gly-Glu-Leu-Val-Trp-Cys-Thr (SEQ ID NO:14), Xaa-Pro-Pro-Cys-Ala-Arg-His-Leu-Gly-Glu-Leu-Val-Trp-Cys-Thr (SEQ ID NO:15), Ala-Pro-Pro-Cys-Ala-Arg-His-Leu-Gly-Glu-Leu-Val-Trp-Cys-Thr (SEQ ID NO:16), Xaa-Pro-Pro-Cys-Ala-Phe-His-Leu-Gly-Glu-Leu-Val-Trp-Cys-Thr (SEQ ID NO:17), or Ala-Pro-Pro-Cys-Ala-Phe-His-Leu-Gly-Glu-Leu-Val-Trp-Cys-Thr (SEQ ID NO:18). Alternatively, a polypeptide can include the amino acid sequence Xaa-Pro-Pro-Asp-Cys-Ala-Trp-His-Leu-Gly-Glu-Leu-Val-Trp-Cys-Thr (SEQ ID NO:19), Ala-Pro-Pro-Asp-Cys-Ala-Trp-His-Leu-Gly-Glu-Leu-Val-Trp-Cys-Thr (SEQ ID NO:20), Xaa-Pro-Pro-Asp-Cys-Ala-Arg-His-Leu-Gly-Glu-Leu-Val-Trp-Cys-Thr (SEQ ID NO:21), Ala-Pro-Pro-Asp-Cys-Ala-Arg-His-Leu-Gly-Glu-Leu-Val-Trp-Cys-Thr (SEQ ID NO:22), Xaa-Pro-Pro-Asp-Cys-Ala-Phe-His-Leu-Gly-Glu-Leu-Val-Trp-Cys-Thr (SEQ ID NO:23), Ala-Pro-Pro-Asp-Cys-Ala-Phe-His-Leu-Gly-Glu-Leu-Val-Trp-Cys-Thr (SEQ ID NO:24), Xaa-Pro-Pro-Arg-Cys-Ala-Trp-His-Leu-Gly-Glu-Leu-Val-Trp-Cys-Thr (SEQ ID NO:25), Ala-Pro-Pro-Arg-Cys-Ala-Trp-His-Leu-Gly-Glu-Leu-Val-Trp-Cys-Thr (SEQ ID NO:26), Xaa-Pro-Pro-Arg-Cys-Ala-Arg-His-Leu-Gly-Glu-Leu-Val-Trp-Cys-Thr (SEQ ID NO:27), Ala-Pro-Pro-Arg-Cys-Ala-Arg-His-Leu-Gly-Glu-Leu-Val-Trp-Cys-Thr (SEQ ID NO:28), Xaa-Pro-Pro-Arg-Cys-Ala-Phe-His-Leu-Gly-Glu-Leu-Val-Trp-Cys-Thr (SEQ ID NO:29), or Ala-Pro-Pro-Arg-Cys-Ala-Phe-His-Leu-Gly-Glu-Leu-Val-Trp-Cys-Thr (SEQ ID NO:30), wherein Xaa at the first position is any amino acid.

The polypeptides provided herein can have a Pro-Pro-Xaa (e.g., Pro-Pro-Ala) sequence at their carboxy termini. For example, a polypeptide can include the amino acid sequence Cys-Ala-Trp-His-Leu-Gly-Glu-Leu-Val-Trp-Cys-Thr-Pro-Pro-Xaa (SEQ ID NO:31), Cys-Ala-Trp-His-Leu-Gly-Glu-Leu-Val-Trp-Cys-Thr-Pro-Pro-Ala (SEQ ID NO:32), Cys-Ala-Arg-His-Leu-Gly-Glu-Leu-Val-Trp-Cys-Thr-Pro-Pro-Xaa (SEQ ID NO:33), Cys-Ala-Arg-His-Leu-Gly-Glu-Leu-Val-Trp-Cys-Thr-Pro-Pro-Ala (SEQ ID NO:34), Cys-Ala-Phe-His-Leu-Gly-Glu-Leu-Val-Trp-Cys-Thr-Pro-Pro-Xaa (SEQ ID NO: 35), Cys-Ala-Phe-His-Leu-Gly-Glu-Leu-Val-Trp-Cys-Thr-Pro-Pro-Ala (SEQ ID NO: 36), Asp-Cys-Ala-Trp-His-Leu-Gly-Glu-Leu-Val-Trp-Cys-Thr-Pro-Pro-Xaa (SEQ ID NO:37), Asp-Cys-Ala-Trp-His-Leu-Gly-Glu-Leu-Val-Trp-Cys-Thr-Pro-Pro-Ala (SEQ ID NO:38), Asp-Cys-Ala-Arg-His-Leu-Gly-Glu-Leu-Val-Trp-Cys-Thr-Pro-Pro-Xaa (SEQ ID NO:39), Asp-Cys-Ala-Arg-His-Leu-Gly-Glu-Leu-Val-Trp-Cys-Thr-Pro-Pro-Ala (SEQ ID NO:40), Asp-Cys-Ala-Phe-His-Leu-Gly-Glu-Leu-Val-Trp-Cys-Thr-Pro-Pro-Xaa (SEQ ID NO:41), Asp-Cys-Ala-Phe-His-Leu-Gly-Glu-Leu-Val-Trp-Cys-Thr-Pro-Pro-Ala (SEQ ID NO:42), Arg-Cys-Ala-Trp-His-Leu-Gly-Glu-Leu-Val-Trp-Cys-Thr-Pro-Pro-Xaa (SEQ ID NO:43), Arg-Cys-Ala-Trp-His-Leu-Gly-Glu-Leu-Val-Trp-Cys-Thr-Pro-Pro-Ala (SEQ ID NO:44), Arg-Cys-Ala-Arg-His-Leu-Gly-Glu-Leu-Val-Trp-Cys-Thr-Pro-Pro-Xaa (SEQ ID NO:45), Arg-Cys-Ala-Arg-His-Leu-Gly-Glu-Leu-Val-Trp-Cys-Thr-Pro-Pro-Ala (SEQ ID NO:46), Arg-Cys-Ala-Phe-His-Leu-Gly-Glu-Leu-Val-Trp-Cys-Thr-Pro-Pro-Xaa (SEQ ID NO:47), or Arg-Cys-Ala-Phe-His-Leu-Gly-Glu-Leu-Val-Trp-Cys-Thr-Pro-Pro-Ala (SEQ ID NO:48), wherein Xaa can be any amino acid.

In some embodiments, the polypeptides provided herein can include additional amino acid sequences at the amino terminus of the sequence set forth in SEQ ID NO:1, the carboxy terminus of the sequence set forth in SEQ ID NO:1, or both. For example, a polypeptide can contain the amino acid sequence Trp-Glu-Ala-$Xaa_1$-Cys-Ala-$Xaa_2$-His-$Xaa_3$-$Xaa_4$-$Xaa_5$-Leu-Val-Trp-Cys-$Xaa_6$-Lys-Val-Glu-Glu (SEQ ID NO:49), wherein the residues denoted by $Xaa_n$ can display variability. As for the amino acid sequence set forth in SEQ ID NO:1, $Xaa_1$ can be absent or can be any amino acid (e.g., Arg or Asp); $Xaa_2$ can be Phe, Tyr, 5-HTP, Trp, or Arg; $Xaa_3$ can be any amino acid; $Xaa_4$ can be Gly or Ala; $Xaa_5$ can be Glu or Ala; and $Xaa_6$ can be absent or can be any amino acid. In one embodiment, a polypeptide can include the amino acid sequence Trp-Glu-Ala-Asp-Cys-Ala-Xaa-His-Leu-Gly-Glu-Leu-Val-Trp-Cys-Thr-Lys-Val-Glu-Glu (SEQ ID NO:50), where Xaa is Arg, Trp, 5-HTP, Tyr, or Phe. For example, a polypeptide can include the amino acid sequence Trp-Glu-Ala-Asp-Cys-Ala-Trp-His-Leu-Gly-Glu-Leu-Val-Trp-Cys-Thr-Lys-Val-Glu-Glu (SEQ ID NO:51).

In another embodiment, a polypeptide can consist of the amino acid sequence $(Xaa_1)_m$-$Xaa_2$-Cys-Ala-$Xaa_3$-His-$Xaa_4$-$Xaa_5$-$Xaa_6$-Leu-Val-Trp-Cys-$(Xaa_7)_n$ (SEQ ID NO:52), wherein the residues denoted by Xaa can display variability, and m and n can be, independently, integers from 0 to 10 (e.g., 0, 1, 2, 3, 4, 5, 6, 7, 8, 9, or 10). For example, $Xaa_1$ can be any amino acid; $Xaa_2$ can be absent or can be any amino acid (e.g., Arg or Asp); $Xaa_3$ can be Phe, Tyr, 5-HTP, Trp, or Arg; $Xaa_4$ can be any amino acid; $Xaa_5$ can be Gly or Ala; $Xaa_6$ can be Glu or Ala; $Xaa_7$ can be any amino acid; and m and n can be from 0 to 5 (e.g., 0, 1, 2, 3, 4, or 5). Alternatively, a polypeptide can consist of the amino acid sequence $(Xaa_1)_m$-Cys-Ala-$Xaa_2$-His-Leu-Gly-Glu-Leu-Val-Trp-Cys-Thr-$(Xaa_3)_n$ (SEQ ID NO:53), wherein $Xaa_1$ is any amino acid, $Xaa_2$ is Phe or Arg, $Xaa_3$ is any amino acid, and m and n are, independently, integers from 0 to 5 (e.g., 0, 1, 2, 3, 4, or 5). Examples of polypeptides within these embodiments, without limitation, include polypeptides consisting of the amino acid sequence Ala-Ala-Ala-Ala-Ala-Asp-Cys-Ala-Arg-His-Leu-Gly-Glu-Leu-Val-Trp-Cys-Ala-Ala-Ala-Ala-Ala (SEQ ID NO:54), Ala-Ala-Arg-Cys-Ala-Arg-His-Leu-Gly-Glu-Leu-Val-Trp-Cys-Thr-Ala-Ala (SEQ ID NO:55), or Ala-Ala-Ala-Asp-Cys-Ala-Phe-Trp-His-Leu-Gly-Glu-Leu-Val-Trp-Cys-Thr-Ala-Ala (SEQ ID NO:56).

The amino acid sequences of the polypeptides described herein typically contain two cysteine residues. Polypeptides containing these amino acid sequences can cyclize due to formation of a disulfide bond between the two cysteine residues. A person having ordinary skill in the art can, for example, use Ellman's Reagent to determine whether a peptide containing multiple cysteine residues is cyclized. In some embodiments, these cysteine residues can be substituted with other natural or non-natural amino acid residues that can form lactam bonds rather than disulfide bonds. For example, one cysteine residue could be replaced with aspartic acid or glutamic acid, while the other could be replaced with ornithine or lysine. Any of these combinations could yield a lactam bridge. By varying the amino acids that form a lactam bridge, a polypeptide provided herein can be generated that contains a bridge approximately equal in length to the disulfide bond that would be formed if two cysteine residues were present in the polypeptide.

The polypeptides provided herein can contain an amino acid tag. A "tag" is generally a short amino acid sequence that provides a ready means of detection or purification through interactions with an antibody against the tag or through other compounds or molecules that recognize the tag. For example, tags such as c-myc, hemagglutinin, polyhistidine, or FLAG® (an eight amino acid peptide tag; Sigma-Aldrich Corp., St. Louis, Mo.) can be used to aid purification and detection of a polypeptide. As an example, a polypeptide with a polyhistidine tag can be purified based on the affinity of histidine residues for nickel ions (e.g., on a Ni—NTA column), and can be detected in western blots by an antibody against polyhistidine (e.g., the Penta-His antibody; Qiagen, Valencia, Calif.). Tags can be inserted anywhere within the polypeptide sequence, although insertion at the amino- or carboxy-terminus is particularly useful.

The term "amino acid" refers to natural amino acids, unnatural amino acids, and amino acid analogs, all in their D and L stereoisomers if their structures so allow. Natural amino acids include alanine (Ala), arginine (Arg), asparagine (Asn), aspartic acid (Asp), cysteine (Cys), glutamine (Gln), glutamic acid (Glu), glycine (Gly), histidine (H is), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Unnatural amino acids include, but are not limited to 5-Hydroxytrpophan, azetidin-ecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native polypeptides, but differs in composition such that either the C-terminal carboxy group, the N-terminal amino group, or the side-chain functional group has been chemically modified to another functional group. Amino acid analogs include natural and unnatural amino acids which are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring, or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine Other examples of amino acids and amino acids analogs are listed in Gross and Meienhofer, *The Peptides: Analysis, Synthesis, Biology*, Academic Press, Inc., New York (1983).

The stereochemistry of a polypeptide can be described in terms of the topochemical arrangement of the side chains of the amino acid residues about the polypeptide backbone, which is defined by the peptide bonds between the amino acid residues and the α-carbon atoms of the bonded residues. In addition, polypeptide backbones have distinct termini and thus direction. The majority of naturally occurring amino acids are L-amino acids. Naturally occurring polypeptides are largely comprised of L-amino acids.

D-amino acids are the enantiomers of L-amino acids and can form peptides that are herein referred to as "inverso" polypeptides (i.e., peptides corresponding to native peptides but made up of D-amino acids rather than L-amino acids). A "retro" polypeptide is made up of L-amino acids, but has an amino acid sequence in which the amino acid residues are assembled in the opposite direction of the native peptide sequence.

"Retro-inverso" modification of naturally occurring polypeptides involves the synthetic assembly of amino acids with α-carbon stereochemistry opposite to that of the corresponding L-amino acids (i.e., D- or D-allo-amino acids), in reverse order with respect to the native polypeptide sequence. A retro-inverso analog thus has reversed termini and reversed direction of peptide bonds, while approximately maintaining the topology of the side chains as in the native peptide sequence. The term "native" refers to any sequence of L-amino acids used as a starting sequence for the preparation of partial or complete retro, inverso or retro-inverso analogs.

Partial retro-inverso polypeptide analogs are polypeptides in which only part of the sequence is reversed and replaced with enantiomeric amino acid residues. Since the retro-inverted portion of such an analog has reversed amino and carboxyl termini, the amino acid residues flanking the retro-inverted portion can be replaced by side-chain-analogous α-substituted geminal-diaminomethanes and malonates, respectively. Alternatively, a polypeptide can be a complete retro-inverso analog, in which the entire sequence is reversed and replaced with D-amino acids.

This document also provides peptidomimetic compounds that are designed on the basis of the amino acid sequences of polypeptides. Peptidomimetic compounds are synthetic, non-peptide compounds having a three-dimensional conformation (i.e., a "peptide motif,") that is substantially the same as the three-dimensional conformation of a selected peptide, and can thus confer the same or similar function as the selected peptide. Peptidomimetic compounds can be designed to mimic any of the polypeptides provided herein.

Peptidomimetic compounds that are protease resistant are particularly useful. Furthermore, peptidomimetic compounds may have additional characteristics that enhance therapeutic utility, such as increased cell permeability and prolonged biological half-life. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, reduced carbonyl, dimethylene and ketomethylene) are known in the art to be useful substitutes for peptide bonds in the construction of peptidomimetic compounds.

The interactions between a polypeptide as described herein and an immunoglobulin molecule typically occur through the $C_H2$-$C_H3$ cleft of the immunoglobulin. Such interactions are engendered through physical proximity and are mediated by, for example, hydrophobic interactions. The "binding affinity" of a polypeptide for an immunoglobulin molecule refers to the strength of the interaction between the polypeptide and the immunoglobulin. Binding affinity typically is expressed as an equilibrium dissociation constant ($K_d$), which is calculated as $K_d=k_{off}/k_{on}$, where $k_{off}$=the kinetic dissociation constant of the reaction, and $k_{on}$=the kinetic association constant of the reaction. $K_d$ is expressed as a concentration, with a low $K_d$ value (e.g., less than 100 nM) signifying high affinity. Polypeptides that can interact with an immunoglobulin molecule typically have a binding affinity of at least 1 μM (e.g., at least 500 nM, at least 100 nM, at least 50 nM, or at least 10 nM) for the $C_H2$-$C_H3$ cleft of the immunoglobulin.

Polypeptides provided herein can bind with substantially equivalent affinity to immunoglobulin molecules that are bound by antigen and to monomeric immunoglobulins. Alternatively, the polypeptides described herein can have a higher binding affinity (e.g., at least 10-fold, at least 100-fold, or at least 1000-fold higher binding affinity) for immunoglobulin molecules that are bound by antigen than for monomeric immunoglobulins. Conformational changes that occur within the Fc region of an immunoglobulin molecule upon antigen binding to the Fab region are likely involved in a difference in affinity. The crystal structures of bound and unbound NC6.8 Fab (from a murine monoclonal antibody) showed that the tail of the Fab heavy chain was displaced by 19 angstroms in crystals of the antigen/antibody complex, as compared to its position in unbound Fab (Guddat et al. (1994) *J. Mol. Biol.* 236-247-274). Since the C-terminal tail of the Fab region is connected to the Fc region in an intact antibody, this shift would be expected to affect the conformation of the $C_H2$-$C_H3$ cleft. Furthermore, examination of several three-dimensional structures of intact immunoglobulins revealed a direct physical connection between the Fab heavy chain and the Fc $C_H2$-$C_H3$ cleft (Harris et al. (1997) *Biochemistry* 36:1581-1597; Saphire et al. (2001) *Science* 293:1155-1159).

Molecular modeling of the $C_H2$-$C_H3$ cleft of monomeric (i.e., unbound) and immune-complexed IgG reveal that the monomeric Fc $C_H2$-$C_H3$ cleft has a closed configuration, which can prevent binding to critical amino acid residues (e.g., H is 435; see, for example, O'Brien et al. (1994) *Arch. Biochem. Biophys.* 310:25-31; Jefferies et al. (1984) *Immunol. Lett.* 7:191-194; and West et al. (2000) *Biochemistry* 39:9698-9708). Immune-complexed (antigen-bound) IgG, however, has a more open configuration and thus is more conducive to ligand binding. The binding affinity of RF for immune-complexed IgG, for example, is much greater than the binding affinity of RF for monomeric IgG (Corper et al.

(1997) *Nat. Struct. Biol.* 4:374; Sohi et al. (1996) *Immunol.* 88:636). The same typically is true for the polypeptides provided herein.

Because the polypeptides described herein can bind to the $C_H2$-$C_H3$ cleft of immunoglobulin molecules, they can be useful for blocking the interaction of other factors (e.g., FcRn, FcR, C1q, histones, MBP, SOD1 and other immunoglobulins) to the Fc region of the immunoglobulin, and thus can inhibit Fc-mediated immune complex formation. By "inhibit" is meant that Fc-mediated immune complex formation is reduced in the presence of a polypeptide provided herein, as compared to the level of immune complex formation in the absence of the polypeptide. Such inhibiting can occur in vitro (e.g., in a test tube) or in vivo (e.g., in an individual). Any suitable method can be used to assess the level of immune complex formation. Many such methods are known in the art, and some of these are described herein.

The polypeptides described herein typically interact with the $C_H2$-$C_H3$ cleft of an immunoglobulin molecule in a monomeric fashion (i.e., interact with only one immunoglobulin molecule and thus do not link two or more immunoglobulin molecules together) with a 1:2 IgG Fc to peptide stoichiometry. Interactions with other immunoglobulin molecules through the Fc region therefore are precluded by the presence of the polypeptide. The inhibition of Fc-mediated immune complex formation can be assessed in vitro, for example, by incubating an IgG molecule with a labeled immunoglobulin molecule (e.g., a fluorescently or enzyme (ELISA) labeled Fc Receptor or C1q in the presence and absence of a polypeptide, and measuring the amount of labeled immunoglobulin that is incorporated into an immune complex. Other methods suitable for detecting immune complex formation also may be used, as discussed below.

Preparation and Purification of Polypeptides

Polypeptides can be produced by a number of methods, many of which are well known in the art. By way of example and not limitation, a polypeptide can be obtained by extraction from a natural source (e.g., from isolated cells, tissues or bodily fluids), by expression of a recombinant nucleic acid encoding the polypeptide (as, for example, described below), or by chemical synthesis (e.g., by solid-phase synthesis or other methods well known in the art, including synthesis with an ABI peptide synthesizer; Applied Biosystems, Foster City, Calif.). Methods for synthesizing retro-inverso polypeptide analogs (Bonelli et al. (1984) *Int. J. Peptide Protein Res.* 24:553-556; and Verdini and Viscomi (1985) *J. Chem. Soc. Perkin Trans.* 1:697-701), and some processes for the solid-phase synthesis of partial retro-inverso peptide analogs also have been described (see, for example, European Patent number EP0097994).

This document provides isolated nucleic acid molecules encoding the polypeptides described herein. As used herein, "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). The term "isolated" as used herein with reference to a nucleic acid refers to a naturally-occurring nucleic acid that is not immediately contiguous with both of the sequences with which it is immediately contiguous (one at the 5' end and one at the 3' end) in the naturally-occurring genome of the organism from which it is derived. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences that is normally immediately contiguous with the DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

This document also provides vectors containing the nucleic acids described herein. As used herein, a "vector" is a replicon, such as a plasmid, phage, or cosmid, into which another DNA segment may be inserted so as to bring about the replication of the inserted segment. Polypeptides can be developed using phage display, for example. Methods well known to those skilled in the art may use phage display to develop the polypeptides described herein. The vectors can be, for example, expression vectors in which the nucleotides encode the polypeptides provided herein with an initiator methionine, operably linked to expression control sequences. As used herein, "operably linked" means incorporated into a genetic construct so that expression control sequences effectively control expression of a coding sequence of interest. An "expression control sequence" is a DNA sequence that controls and regulates the transcription and translation of another DNA sequence, and an "expression vector" is a vector that includes expression control sequences, so that a relevant DNA segment incorporated into the vector is transcribed and translated. A coding sequence is "operably linked" and "under the control" of transcriptional and translational control sequences in a cell when RNA polymerase transcribes the coding sequence into mRNA, which then is translated into the protein encoded by the coding sequence.

Methods well known to those skilled in the art may be used to subclone isolated nucleic acid molecules encoding polypeptides of interest into expression vectors containing relevant coding sequences and appropriate transcriptional/translational control signals. See, for example, Sambrook et al., *Molecular Cloning: A Laboratory Manual* ($2^{nd}$ edition), Cold Spring Harbor Laboratory, New York (1989); and Ausubel et al., *Current Protocols in Molecular Biology*, Green Publishing Associates and Wiley Interscience, New York (1989). Expression vectors can be used in a variety of systems (e.g., bacteria, yeast, insect cells, and mammalian cells), as described herein. Examples of suitable expression vectors include, without limitation, plasmids and viral vectors derived from, for example, herpes viruses, retroviruses, vaccinia viruses, adenoviruses, and adeno-associated viruses. A wide variety of suitable expression vectors and systems are commercially available, including the pET series of bacterial expression vectors (Novagen, Madison, Wis.), the Adeno-X expression system (Clontech), the Baculogold baculovirus expression system (BD Biosciences Pharmingen, San Diego, Calif.), and the pCMV-Tag vectors (Stratagene, La Jolla, Calif.).

Expression vectors that encode the polypeptides described herein can be used to produce the polypeptides. Expression systems that can be used for small or large scale production of polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules provided herein; yeast (e.g., *S. cerevisiae*) transformed with recombinant yeast expression vectors containing the nucleic acid molecules of the invention; insect cell systems infected with recombinant virus expression vectors (e.g., baculovirus) containing the nucleic acid molecules provided herein; plant cell systems infected with recombinant virus expression vectors (e.g., tobacco mosaic virus) or transformed with recombinant plasmid expression vectors (e.g., Ti plasmid) containing the nucleic acid molecules provided herein; or mammalian cell systems (e.g., primary cells or immortalized cell lines such as COS cells, CHO cells, HeLa cells, HEK 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids provided herein.

The term "purified polypeptide" as used herein refers to a polypeptide that either has no naturally occurring counterpart (e.g., a peptidomimetic), or has been chemically synthesized and is thus uncontaminated by other polypeptides, or that has been separated or purified from other cellular components by which it is naturally accompanied (e.g., other cellular proteins, polynucleotides, or cellular components). Typically, the polypeptide is considered "purified" when it is at least 70%, by dry weight, free from the proteins and naturally occurring organic molecules with which it naturally associates. A preparation of purified polypeptide therefore can be, for example, at least 80%, at least 90%, or at least 99%, by dry weight, the polypeptide. Suitable methods for purifying polypeptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

Methods of modeling, designing, and identifying compounds

This document provides methods for designing, modeling, and identifying compounds that can bind to the $C_H2$-$C_H3$ cleft of an immunoglobulin molecule and thus serve as inhibitors of Fc-mediated immune complex formation. Such compounds also are referred to herein as "ligands." Compounds designed, modeled, and identified by these methods typically can interact with an immunoglobulin molecule through the $C_H2$-$C_H3$ cleft, and typically have a binding affinity of at least 1 μM (e.g., at least 500 nM, at least 100 nM, at least 50 nM, or at least 10 nM) for the $C_H2$-$C_H3$ cleft of the immunoglobulin. Such compounds generally have higher binding affinity (e.g., at least 10-fold, at least 100-fold, or at least 1000-fold higher binding affinity) for immune-complexed immunoglobulin molecules than for monomeric immunoglobulin molecules.

Compounds typically interact with the $C_H2$-$C_H3$ cleft of an immunoglobulin molecule in a monomeric fashion (i.e., interact with only one immunoglobulin molecule and thus do not link two or more immunoglobulin molecules together). The interactions between a compound and an immunoglobulin molecule typically involve the amino acid residues at positions 252, 253, 435, and 436 of the immunoglobulin (number according to Kabat, supra). For example, SEQ ID NO:20 (NB-406) may have hydrophobic packing with IgG Fc Met-252, Ile-253, Ser-254, His-435 and Tyr-436 (e.g., the indole ring of Trp-14 in SEQ ID NO:20 can have a hydrophobic interaction with IgG Fc His-435). Alanine substitution of IgG Fc Asn-434, His-435 or Tyr-436 can disrupt binding ($\Delta\Delta G \geq 1.5$ kcal/mol). In addition, alanine substitution of SEQ ID NO:20 Val-13 or Trp-14 can result in disruption of binding ($\Delta\Delta G \geq 2.0$ kcal/mol).

The interaction between compounds and the $C_H2$-$C_H3$ cleft renders the compounds capable of inhibiting the Fc-mediated formation of immune complexes by blocking the binding of other factors (e.g., Fc:Fc interactions, FcγRs, FcRn, histones, MBP, MOG, RF, Tau protein, α-synuclein, SOD 1, TNF and C1q) to the $C_H2$-$C_H3$ cleft.

Compounds identified by the methods provided herein can be polypeptides such as, for example, those described herein. Alternatively, a compound can be any suitable type of molecule that can specifically bind to the $C_H2$-$C_H3$ cleft of an immunoglobulin molecule.

By "modeling" is meant quantitative and/or qualitative analysis of receptor-ligand structure/function based on three-dimensional structural information and receptor-ligand interaction models. This includes conventional numeric-based molecular dynamic and energy minimization models, interactive computer graphic models, modified molecular mechanics models, distance geometry and other structure-based constraint models. Modeling typically is performed using a computer and may be further optimized using known methods.

Methods of designing ligands that bind specifically (i.e., with high affinity) to the $C_H2$-$C_H3$ cleft of an immunoglobulin molecule having bound antigen typically are computer-based, and involve the use of a computer having a program capable of generating an atomic model. Computer programs that use X-ray crystallography data are particularly useful for designing ligands that can interact with an Fc $C_H2$-$C_H3$ cleft. Programs such as RasMol, for example, can be used to generate a three dimensional model of a $C_H2$-$C_H3$ cleft and/or determine the structures involved in ligand binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Methods can include, for example, providing to a computer the atomic structural coordinates for amino acid residues within the $C_H2$-$C_H3$ cleft (e.g., amino acid residues at positions 252, 253, 435, and 436 of the cleft) of an immunoglobulin molecule in an Fc-mediated immune complex, using the computer to generate an atomic model of the $C_H2$-$C_H3$ cleft, further providing the atomic structural coordinates of a candidate compound and generating an atomic model of the compound optimally positioned within the $C_H2$-$C_H3$ cleft, and identifying the candidate compound as a ligand of interest if the compound interacts with the amino acid residues at positions 252, 253, 435, and 436 of the cleft. The data provided to the computer also can include the atomic coordinates of amino acid residues at positions in addition to 252, 253, 435, and 436. By "optimally positioned" is meant positioned to optimize hydrophobic interactions between the candidate compound and the amino acid residues at positions 252, 253, 435, and 436 of the $C_H2$-$C_H3$ cleft.

Alternatively, a method for designing a ligand having specific binding affinity for the $C_H2$-$C_H3$ cleft of an immunoglobulin molecule can utilize a computer with an atomic model of the cleft stored in its memory. The atomic coordinates of a candidate compound then can be provided to the computer, and an atomic model of the candidate compound optimally positioned can be generated. As described herein, a candidate compound can be identified as a ligand having specific binding affinity for the $C_H2$-$C_H3$ cleft of an immunoglobulin molecule if, for example, the compound interacts with the amino acid residues at positions 252, 253, 435, and 436 of the cleft.

Such methods have shown that monomeric (non-antigen bound) IgG Fc binds at a site distinct from the IgG Fc $C_H2$-$C_H3$ cleft, such as the lower hinge region (Wines et al. (2000) *J. Immunol.* 164:5313-5318), while immune complexed (antigen bound) IgG Fc binding to FcγIIa is inhibited by an IgM rheumatoid factor (RF-AN), which has been shown by 3D structure to only bind to the IgG Fc $C_H2$-$C_H3$ interface cleft (Sohi et al. (1996) *Immunology* 88:636-641; and Corper et al. (1997) *Nature Struct. Biol.* 4(5):374-381). Soluble FcγIIa inhibits the binding of immune complexed (but not monomeric, non-immune complexed) IgG Fc to RF-AN (Wines et al. (2003) *Immunol.* 109:246-254), and inhibitors that bind to the IgG Fc $C_H2$-$C_H3$ cleft, such as the peptides described herein, inhibit the binding of immune complexed (antigen-bound) IgG Fc to FcγRs.

Compounds also can be interactively designed from structural information of the compounds described herein using other structure-based design/modeling techniques (see, e.g., Jackson (1997) *Seminars in Oncology* 24:L164-172; and Jones et al. (1996) *J. Med. Chem.* 39:904-917).

Compounds and polypeptides also can be identified by, for example, identifying candidate compounds by computer mo as fitting spatially and preferentially (i.e., with high affinity) into the $C_H2$-$C_H3$ cleft of an immunoglobulin molecule, and then screening those compounds in vitro or in vivo for the ability to inhibit Fc-mediated immune complex formation. Suitable methods for such in vitro and in vivo screening include those described herein.

Compositions and Articles of Manufacture

This document provides compositions and articles of manufacture that can be used in methods for treating conditions that arise from abnormal Fc-mediated immune complex formation (e.g., over-production of Fc-mediated immune complexes). The polypeptides, compounds, and compositions provided herein can be administered to a subject (e.g., a human or another mammal) having an viral infection, for example, that can be alleviated by modulating Fc-mediated immune complex formation and inhibit immune complexed IgG Fc to mC1q, sC1q, FcγRs, and FcRn. Typically, one or more polypeptides or compounds can be administered to a subject suspected of having a disease or condition associated with immune complex formation. Compositions generally contain one or more polypeptides and compounds described herein. A $C_H2$-$C_H3$ binding polypeptide, for example, can be in a pharmaceutically acceptable carrier or diluent, and can be administered in amounts and for periods of time that will vary depending upon the nature of the particular disease, its severity, and the subject's overall condition. Typically, the polypeptide is administered in an inhibitory amount (i.e., in an amount that is effective for inhibiting the production of immune complexes in the cells or tissues contacted by the polypeptide). The polypeptides and methods described herein also can be used prophylactically, e.g., to minimize immunoreactivity in a subject at risk for abnormal or over-production of immune complexes (e.g., a transplant recipient).

The ability of a polypeptide to inhibit Fc-mediated immune complex formation can be assessed by, for example, measuring immune complex levels in a subject before and after treatment. A number of methods can be used to measure immune complex levels in tissues or biological samples, including those that are well known in the art. If the subject is a research animal, for example, immune complex levels in the joints can be assessed by immunostaining following euthanasia. The effectiveness of an inhibitory polypeptide also can be assessed by direct methods such as measuring the level of circulating immune complexes in serum samples. Alternatively, indirect methods can be used to evaluate the effectiveness of polypeptides in live subjects. For example, reduced immune complex formation can be inferred from clinical improvement of immune mediated diseases or in vitro or in vivo models of which have been shown to be essential in the therapeutic use in treating Atherosclerosis.

Methods for formulating and subsequently administering therapeutic compositions are well known to those skilled in the art. Dosing is generally dependent on the severity and responsiveness of the disease state to be treated, with the course of treatment lasting from several days to several months, or until a cure is effected or a diminution of the disease state is achieved. Persons of ordinary skill in the art routinely determine optimum dosages, dosing methodologies and repetition rates. Optimum dosages can vary depending on the relative potency of individual polypeptides, and can generally be estimated based on EC50 found to be effective in in vitro and in vivo animal models. Typically, dosage is from 0.01 μg to 100 g per kg of body weight, and may be given once or more daily, biweekly, weekly, monthly, or even less often. Following successful treatment, it may be desirable to have the patient undergo maintenance therapy to prevent the recurrence of the disease state.

The present document provides pharmaceutical compositions and formulations that include the polypeptides and/or compounds described herein. Polypeptides therefore can be admixed, encapsulated, conjugated or otherwise associated with other molecules, molecular structures, or mixtures of compounds such as, for example, liposomes, polyethylene glycol, receptor targeted molecules, or oral, rectal, topical or other formulations, for assisting in uptake, distribution and/or absorption.

A "pharmaceutically acceptable carrier" (also referred to herein as an "excipient") is a pharmaceutically acceptable solvent, suspending agent, or any other pharmacologically inert vehicle for delivering one or more therapeutic compounds (e.g., $C_H2$-$C_H3$ binding polypeptides) to a subject. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions can be administered by a number of methods, depending upon whether local or systemic treatment is desired and upon the area to be treated. Administration can be, for example, topical (e.g., transdermal, sublingual, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). For treating tissues in the central nervous system, $C_H2$-$C_H3$ binding polypeptides can be administered by injection or infusion into the cerebrospinal fluid, preferably with one or more agents capable of promoting penetration of the polypeptides across the blood-brain barrier.

Formulations for topical administration of $C_H2$-$C_H3$ binding polypeptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays are particularly useful, and can be administered by, for example, a nebulizer or another nasal spray device. Administration by an inhaler also is particularly useful. Conventional pharmaceutical carriers, aqueous, powder or oily bases, thickeners and the like may be necessary or desirable.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including LIPOFECTIN® (a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in membrane-filtered water; Invitrogen/Life Technologies, Carlsbad, Calif.) and EFFECTENE™ (a non-liposomal lipid formulation in conjunction with a DNA-condensing enhancer; Qiagen, Valencia, Calif.).

Polypeptides can further encompass any pharmaceutically acceptable salts, esters, or salts of such esters, or any other compound which, upon administration to an animal including a human, is capable of providing (directly or indirectly) the biologically active metabolite or residue thereof. Accordingly, for example, this document provides pharmaceutically acceptable salts of polypeptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the polypeptides provided herein (i.e., salts that retain the desired biological activity of the parent polypeptide without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); and salts formed with organic acids (e.g., acetic acid, citric acid, oxalic acid, palmitic acid, or fumaric acid).

Pharmaceutical compositions containing the polypeptides provided herein also can incorporate penetration enhancers that promote the efficient delivery of polypeptides to the skin of animals. Penetration enhancers can enhance the diffusion of both lipophilic and non-lipophilic drugs across cell membranes. Penetration enhancers can be classified as belonging to one of five broad categories, i.e., surfactants (e.g., sodium lauryl sulfate, polyoxyethylene-9-lauryl ether and polyoxyethylene-20-cetyl ether); fatty acids (e.g., oleic acid, lauric acid, myristic acid, palmitic acid, and stearic acid); bile salts (e.g., cholic acid, dehydrocholic acid, and deoxycholic acid); chelating agents (e.g., disodium ethylenediaminetetraacetate, citric acid, and salicylates); and non-chelating non-surfactants (e.g., unsaturated cyclic ureas). Alternatively, inhibitory polypeptides can be delivered via iontophoresis, which involves a transdermal patch with an electrical charge to "drive" the polypeptide through the dermis.

Some embodiments provided herein include pharmaceutical compositions containing (a) one or more polypeptides and (b) one or more other agents that function by a different mechanism. For example, anti-inflammatory drugs, including but not limited to nonsteroidal anti-inflammatory drugs and corticosteroids, and antiviral drugs, including but not limited to ribivirin, vidarabine, acyclovir and ganciclovir, can be included in compositions. Other non-polypeptide agents (e.g., chemotherapeutic agents) also are within the scope of this document. Such combined compounds can be used together or sequentially.

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

The pharmaceutical formulations, which can be presented conveniently in unit dosage form, can be prepared according to conventional techniques well known in the pharmaceutical industry. Such techniques include the step of bringing into association the active ingredients (e.g., the $C_H2$-$C_H3$ binding polypeptides provided herein) with the desired pharmaceutical carrier(s) or excipient(s). Typically, the formulations can be prepared by uniformly and bringing the active ingredients into intimate association with liquid carriers or finely divided solid carriers or both, and then, if necessary, shaping the product. Formulations can be sterilized if desired, provided that the method of sterilization does not interfere with the effectiveness of the polypeptide contained in the formulation.

The compositions described herein can be formulated into any of many possible dosage forms such as, but not limited to, tablets, capsules, liquid syrups, soft gels, suppositories, and enemas. The compositions also can be formulated as suspensions in aqueous, non-aqueous or mixed media. Aqueous suspensions further can contain substances that increase the viscosity of the suspension including, for example, sodium carboxymethylcellulose, sorbitol, and/or dextran. Suspensions also can contain stabilizers.

$C_H2$-$C_H3$ binding polypeptides can be combined with packaging material and sold as kits for reducing Fc-mediated immune complex formation. Components and methods for producing articles of manufacture are well known. The articles of manufacture may combine one or more of the polypeptides and compounds set out in the above sections. In addition, the article of manufacture further may include, for example, buffers or other control reagents for reducing or monitoring reduced immune complex formation. Instructions describing how the polypeptides are effective for reducing Fc-mediated immune complex formation can be included in such kits.

Dengue Fever

Dengue Fever is the most prevalent mosquito-borne viral illness in the world, with more than 2.5 billion people at risk of infection in tropical regions. Dengue is transmitted to humans primarily by the urban-dwelling *Aedes aegypti* mosquito (also designated as *Stegomyia aegypti*, which also transmits the yellow fever virus. World War II era programs to eliminate yellow fever had the added benefit of controlling Dengue in targeted areas. In the past three decades, however, cessation of these programs and rapid urbanization in tropical areas has allowed Dengue to re-emerge.

The dengue virus (DENV) has four serotypes, each capable of infecting the same person. Dengue infections can be asymptomatic or can cause a spectrum of symptoms, ranging from a debilitating fever to a potentially fatal Dengue Hemorrhagic Fever (DHF) and Dengue Shock Syndrome (DSS). About 1% of Dengue Fever cases progress to DHF.

An in vivo model of Dengue Fever was generated by xenografting neonatal RAG2-/-γc-/-mice with human CD34+ hematopoietic stem cells, resulting in de novo development of major functional cells of the human adaptive immune system (Kuruvilla et al. (2007) *Virol.* 369:143-152). To evaluate susceptibility to DENV infection, the humanized mice were challenged with DEN-2 serotype. Viremia lasting up to 3 weeks was detected in infected mice with viral titers reaching up to $10^{6.3}$ RNA copies/ml, and fever characteristic of dengue also was noted. In addition, an antibody capture ELISA to evaluate the presence of human anti-dengue antibodies showed anti-dengue IgM by 2 weeks post-infection, followed by IgG at 6 weeks. Sera from some of the infected mice also were found to be capable of dengue virus neutralization.

Macrophages are important in dengue pathogenesis, but the initiation of DENV infections appears to begin before the involvement of macrophages. In particular, dendritic cells (DC) have been shown to by 10-fold more permissive for DENV infection than monocytes or macrophages. Mast cells also are present in dermal and subdermal tissues, which would be expected to come into contact with Dengue Virons shortly after a mosquito bite. In addition to DC and blood monocytes and macrophages, mast cells are susceptible to antibody-enhanced dengue virus infection, producing a number of inflammatory mediators (e.g., IL-1, IL-6, and CCL5). The participating FcRs in antibody-enhanced mast cell dengue virus infection appear to be FcγRIIa/b. As shown in Table 3 of Example 2 herein, SEQ ID NO:20 was about 90% effective in blocking the binding of immune complexes to FcγRIIa/b. Thus, polypeptides such as this may have a significant impact on ADE of DENV infection in DC, mast cells, macrophages, and monocytes.

Circulating immune complexes (CIC) also may play a role in the immunopathogenesis of DHF. CIC have been detected in the serum of DHF patients based on the inhibitory activity of CIC on agglutination of IgG-coated latex particles by C1q (Agnello et al. (1970) *Immunol.* 19:909-919; and Agnello et al. (1971) *J. Exp. Med.* 134:228-241). This latex technique provides a simple, semi-quantitative method which can demonstrate the presence of IC in the serum of patients during the early course of DHF (Ruangjirachuporn et al. (1979) *Clin. Exp. Immunol.* 36:46-53). In addition, large the Raji cell immunofluorescent method (Theophilopoulos (1976) *J. Clin. Invest.* 57:169-82) has shown that large size CIC develop in the later stage of DHF. Removal of these complexes by absorption with Raji cells reduced or eliminated the reactivity in the Raji cell immunofluorescence assay, as well as in the latex technique. Thus, these studies confirmed the specificity of the reaction between the dengue antigen-antibody complexes in DHF serum and the surface of the Raji cells. In addition, virus-containing IC have been shown to persist at defervescence for patients with DHF.

As discussed in Example 3 herein, inactivated DENV2 virons (DENV-2 strain 16681) can avidly bind heterologous, non-DENV-associated, peroxidase-anti-peroxidase immune complexes. A likely reason for the avid binding, based on structural analysis (Zhang et al. (2004) *Structure* 12:1607-1618) is that DENV envelope protein domain III may be responsible for homologous and heterologous IgG immune complex binding. The second weakly IC binding protein is non-structural protein 1 (NS1), which is released in high amounts to the serum of DENV infected individuals and also is found within the DENV viron itself and on the surface of DENV infected cells. The results of DENV NS1 binding to non-DENV related immune complexes (PAP-IC), and the inhibition of NS1 binding to IC by NB406 (SEQ ID NO:20; APPDCAWHLGELVWCT) are shown in Example 6 below. In addition, Table 3 in Example 2 shows that SEQ ID NO:20 inhibited binding of either FcγRIIa or FcγRIIb to immune complexed IgG Fc by more than 90%, suggesting that SEQ ID NO:20 may abrogate ADE in DC caused by sub-neutralizing DENV antibody titers.

Methods for Using $C_H2$-$C_H3$ Binding Polypeptides to Inhibit Fc-Mediated Immune Complex Formation $C_H2$-$C_H3$ binding polypeptides can be used in in vitro assays of Fc-mediated immune complex (IC) formation. Such methods are useful to, for example, evaluate the ability of a $C_H2$-$C_H3$ cleft-binding polypeptide to block Fc-mediated IC formation. In vitro methods can involve, for example, contacting an immunoglobulin molecule (e.g., an antigen bound immunoglobulin molecule) with an effector molecule (e.g., mC1q, sC1q, FcRs and FcRn, or another antibody) in the presence and absence of a polypeptide as provided herein, and determining the level of IC formation in each sample. Levels of IC formation can be evaluated by, for example, polyacrylamide gel electrophoresis with Coomassie blue or silver staining, or by co-immunoprecipitation. Such methods are known to those of ordinary skill in the art, and can be used to test the ability of a candidate polypeptide or compound to inhibit IC formation associated with an infectious viral disease, for example.

Methods provided herein also can be used to inhibit IC formation in a subject, and to treat an infectious viral disease in a subject by inhibiting Fc-mediated IC formation. Such methods can include, for example, administering any of the polypeptides described herein, or a composition containing any of the polypeptides described herein, to a subject having or being at risk for having or developing an infectious viral disease (e.g., Dengue Fever). For example, a method can include administering to an individual a composition containing a polypeptide that includes the amino acid sequence Cys-Ala-Trp-His-Leu-Gly-Glu-Leu-Val-Trp-Cys-Thr (SEQ ID NO:10). Alternatively, a method can include administering to a subject a polypeptide that contains the amino acid sequence Asp-Cys-Ala-Trp-His-Leu-Gly-Glu-Leu-Val-Trp-Cys-Thr (SEQ ID NO:2), Xaa-Pro-Pro-Asp-Cys-Ala-Trp-His-Leu-Gly-Glu-Leu-Val-Trp-Cys-Thr (SEQ ID NO:19; where Xaa is any amino acid), or Ala-Pro-Pro-Asp-Cys-Ala-Trp-His-Leu-Gly-Glu-Leu-Val-Trp-Cys-Thr (SEQ ID NO:20).

In some embodiments, when the viral disease is Dengue Fever, a polypeptide can be administered to inhibit IC formation that is associated with ADE of Dengue Fever or infection by DENV, or contributes to the enhancement of a DENV infection. The polypeptide can, for example, result in clinical or histological improvement of a DENV infection, result in an improvement or delay of onset of one or more of the histiological characteristics of a DENV infection, and/or decrease the ADE of a DENV infection (e.g., a DENV infection such as DHF or DSS). In some cases, the polypeptide can inhibit binding of an anti-DENV heterologous IgG IC to an FcγR, inhibit formation of IC that contribute to immunopathogenesis of the ADE of DENV infections, inhibit binding of DENV virons to IgG IC, inhibit binding of a DENV protein (e.g., NS1) to an IgG immune complex, inhibit binding of TNF-α to IgG IC, inhibit binding of a DENV-IgG IC to FcγI, a FcγIIa H131 allele, a FcγIIa R131 allele, FcγRIIb, FcγRIIc, FcγRIIIa, or FcγγIIIb, and/or inhibit binding of DENV-IgG IC to mC1q or sC1q.

The invention will be further described in the following examples, which do not limit the scope of the invention described in the claims.

EXAMPLES

In Vitro Assays or Measuring Ligand Binding to the $C_H2$-$C_H3$ Cleft

In vitro assays involving enzyme-linked immunosorbent assay (ELISA) have been used to demonstrate (competitive) inhibition of immune complexed IgG Fc binding to immune mediating factors such as FcRs: (FcγRI, FcγIIa, FcγRIIb/c, FcγRIIIa/b), FcRn, mC1q, and sC1q by the polypeptides and compounds described herein. See, e.g., Examples _____ herein, as well as U.S. Patent Publication Nos. 20070225231 and 20070276125, and PCT Publication No. WO2007/030475. Standardized reagents and ELISA kits are useful to reduce costs and increase the reproducibility of the experiments.

In a standard ELISA, an antigen is immunoadsorbed onto a plastic microwell. After suitable blocking and washing, a primary antibody with specificity directed toward the antigen is added to the microwell. After another wash phase, a secondary antibody that is directed toward the primary antibody and conjugated to an enzyme marker such as horseradish peroxidase (HRP) is added to the microwell. Following another wash cycle, the appropriate enzyme substrate is added. If an antigen to primary antibody to secondary antibody/HRP conjugate is formed, the conjugated enzyme catalyzes a colorimetric chemical reaction with the substrate, which is read with a microplate reader or spectrophotometer. By standardizing the levels of the antigen and secondary antibody/HRP conjugate, a titer of the primary antibody (the variable) is established. In a standard ELISA system, the primary antibody binds to the antigen through its complementarity determining regions (CDR) located in the Fab arms. Likewise, the secondary antibody/HRP conjugate binds to the primary antibody via its CDR Fab region. Because the HRP is conjugated to the Fc region of the secondary antibody, direct Fc binding is very limited or abrogated.

For this reason, a "reverse ELISA" technique has been used to assess binding of the Fc region to ligands that bind to immune complexed IgG Fc. In a reverse ELISA, the enzyme (e.g., HRP) is not covalently conjugated to the Fc portion of the secondary antibody. Rather, a preformed immune complex of peroxidase-rabbit (or mouse) anti-peroxidase IgG ("PAP" complex) is used. In this method, HRP serves both as the antigen and the enzyme marker but does not block the Fc region. In the reverse ELISA system, an Fc $C_H2$-$C_H3$ cleft binding ligand (e.g., purified human C1q) was bound to microwell plates. In the absence of competitor, PAP complexes bound to the immobilized ligand and the reaction between HRP and its substrate produces a signal. This signal was reduced by polypeptides and compounds that inhibited PAP binding to the immobilized ligand.

Example 1

Inhibition of C1q Binding

PAP complexes were formed mixing 2 μl of rabbit anti-peroxidase (Sigma Chemicals Product P 7899) with 50 μl of peroxidase (Sigma-Aldrich P6782) in 1 ml distilled water. PAP (100 μl) were pre-incubated with 100 μl of peptide for one hour, 100 μl were pre-incubated with 100 μl of peptide or human C1q (Quidel Corp.) for one hour. The C1q/PAP and peptide/PAP mixtures (100 μl) were incubated with C1q coated plates for 30 minutes. After washing, plates were incubated with ATBS (Quidel Corp.) for 15 minutes and read at 405 nm. Results are shown in Table 1.

TABLE 1

| Peptide | SEQ ID NO: | OD 405 nm |
|---|---|---|
| DCAWHLGELVWCT | 2 | 1.100 |
| APPCARHLGELVWCT | 16 | 0.567 |
| DCAFHLGELVWCT | 3 | 0.859 |

TABLE 1-continued

| Peptide | SEQ ID NO: | OD 405 nm |
|---|---|---|
| APPDCAWHLGELVWCT | 20 | 0.389 |
| APPCAFHLGELVWCT | 18 | 0.983 |
| APPCAWHLGELVWCT | 14 | 1.148 |
| C1q (negative control) | — | 0.337 |
| Positive Control | — | 2.355 |

APPDCAWHLGELVWCT (SEQ ID NO:20) resulted in the greatest inhibition of C1q binding, almost equaling C1q itself. Peptide APPCARHLGELVWCT (SEQ ID NO:16) gave the next best result.

Example 2

Inhibition of FcR Binding to PAP-IC by SEQ ID NO:20

Once the reverse ELISA protocol was established using the C1q assay, the assay was redesigned using FcγIIa, FcγIIb and FcγIII in place of C1q. Highly purified FcγIIa, FcγIIb and FcγIII (R&D Systems, Minneapolis, Minn.) were immunoadsorbed onto plastic microwells. After optimizing the FcγR reverse ELISA system, simple competitive inhibition experiments using polypeptides provided herein were conducted to investigate their ability to inhibit binding of immune complexes to purified FcγR.

Falcon microtiter plates were coated with 1:10 dilutions of highly purified FcγIIa, FcγIIb and FcγIII and incubated for 24 hours. The plates were washed and then blocked with 5×BSA blocking solution (Alpha Diagnostic International, San Antonio, Tex.) for 24 hours. PAP immune complexes were formed as described in Example 1. PAP (100 μl) were pre-incubated with 100 μl of peptide for one hour. PAP/peptide mixtures were added to the FcγR coated plates and incubated for one hour. After washing, plates were incubated with ABTS substrate (Quidel Corp.) for 15 minutes and read at 405 nm. Results are shown in Table 2.

TABLE 2

| | | $OD_{405}$ | | |
|---|---|---|---|---|
| Peptide | SEQ ID | FcγIIa (R131 allele) | FcγIIb | FcγIIIa |
| DCAWHLGELVWCT | 2 | 0.561 | 0.532 | 0.741 |
| APPCARHLGELVWCT | 16 | 0.956 | 0.768 | 0.709 |
| DCAFHLGELVWCT | 3 | 0.660 | 0.510 | 0.810 |
| APPDCAWHLGELVWCT | 20 | 0.509 | 0.496 | 0.670 |
| APPCAFHLGELVWCT | 18 | 0.605 | 0.380 | 0.880 |
| APPCAWHLGELVWCT | 14 | 0.658 | 0.562 | 0.530 |
| Positive Control | — | 1.599 | 1.394 | 1.588 |

Peptide APPDCAWHLGELVWCT (SEQ ID NO:20) appeared to result in the greatest overall inhibition of FcR binding to PAP, followed by peptide DCAWHLGELVWCT (SEQ ID NO:2).

Experiments with SEQ ID NO:20 were repeated. Costar microtiter plates were coated with 1:10 dilutions of highly purified FcγIIa (His 131 allele aka H161), FcγIIb and FcγIIIb and incubated for 24 hours. The plates were washed and then blocked with 10 mg/ml BSA blocking solution for 24 hours. PAP immune complexes were formed as described in Example 2. PAP (100 μl) were pre-incubated with 100 μl of peptide for one hour. PAP/peptide mixtures were added to the FcγR coated plates and incubated for one hour. After washing, plates were incubated with ABTS substrate for 15 minutes and read at 405 nm. Results are shown in Table 3.

TABLE 3

| Peptide | SEQ ID | Fcγ1 | FcγIIa* | FcγIIb/c | FcγIIIb (NA2) |
|---|---|---|---|---|---|
| APPDCAWHLGELVWCT | 20 | 0.264 | 0.209 | 0.266 | 0.266 |
| Positive control | — | 2.333 | 3.509 | 2.218 | 3.060 |
| % inhibition of IC binding | — | 89 | 94 | 88 | 91 |

*Note: (H131 allele)

Thus, SEQ ID NO:20 inhibited binding of all three major classes of Fc receptor (FcγI, FcγIIa/FcγIIb, and FcγIII) to soluble PAP immune complexes.

Example 3

Inactivated DENV2 Virons Bind Non-DENV Immune Complexes

About 1 ng of DENV2 (strain 16681; Microbix Corp.) was coated onto Costar microtiter plates using ELISA coating buffer (Alpha Diagnostic International) for 24 hours at 4° C. After 24 hours, the plates were washed 5 times with ELISA wash solution (Quidel Corp.), and blocked with highly purified BSA for 1 hour. After 5 washes, PAP IC were incubated with the DENV-coated microtiter plates for one hour. After an hour, the plates were again washed 5 times with Quidel ELISA wash solution, and then incubated with ABTS (Immunochem Corp.) for twenty minutes. The higher the $OD_{405\,nm}$, the higher the binding of DENV non-related immune complex (PAP-IC) to DENV2 (16681) virons. Results are shown in Table 4.

TABLE 4

| Sample | 1 | 2 | 3 | 4 |
|---|---|---|---|---|
| PAP-Immune Complexes (n = 4) Avg. = 3.080 (Neg ave. = 0.050) | 3.106 | 3.086 | 3.046 | 3.081 |

Thus, DENV2 (16681) virons bound avidly to non-DENV-related immune complexes, making DENV ADE in non DENV, IC+ individuals possible in DENV endemic areas.

Example 4

Inhibition of DENV-IgG-IC Binding to FcγIIa Coated Plates

Highly purified recombinant human FcγIIa (R&D Systems) was immunoadsorbed onto plastic microwells (Costar Microtiter plates) using ELISA coating buffer (Alpha Diagnostic International) for 24 hours at 4° C. After 24 hours, the plates were washed 5 times with ELISA wash solution (Quidel Corp.), blocked with highly purified BSA for 1 hour, and washed 5 times. Human anti-DENV2 IC. were formed by combining inactivated DENV-2 virons (strain 16681, Microbix Corp.) with neutralizing polyclonal, pooled, affinity-purified IgG from DENV convalescent individuals (Calbiotech Dengue Fever IgG ELISA; Cat. No. DE050G4). The results of 1:250 and 1:500 serial dilutions (ADE was most evident at serum dilutions of 1:250 to 1:500) of the DENV-IgG-IC were tested against inhibition of DENV-IgG-IC binding to huFcγRIIa coated microtiter wells. Results using huFcγRIIa coated wells with either a 1:250 dilution of DENV-IgG-IC with no inhibitor, a 1:250 dilution of DENV-IgG-IC with SEQ ID NO:20, a 1:500 dilution of DENV-IgG-IC with no inhibitor, and a 1:500 dilution of DENV-IgG-IC with SEQ ID NO:20 are shown in Table 5.

TABLE 5

| Sample | SEQ ID | Dilution of DENV2 (16681)-DENV convalescent IgG-IC | |
|---|---|---|---|
| | | 1:250 | 1:500 |
| No peptide inhibitor (+control) | — | 2.885 | 2.362 |
| APPDCAWHLGELVWCT | 20 | 0.265 | 0.289 |

Thus, SEQ ID NO:20 showed a marked ability to inhibit binding of IC comprised of inactivated DENV2 (strain 16681)-anti-DENV polyclonal convalescent IgG-IC to FcγIIa Coated Plates. The DENV-anti-DENV (heterologous) polyclonal convalescent IgG-IC binding to FcγIIa is considered to be the primary immunological mechanism leading to ADE of Dengue Fever infections and the leading cause of the more serious, possibly life threatening DHF/DSS, making SEQ ID NO:20 a candidate therapeutic for treatment and/or prevention of DHF/DSS.

Example 5

Inhibition of Non-DENV IC (PAP-IC) Binding to DENV NS1

Highly purified recombinant DENV (100 μg Dengue Virus recombinant NS1; Prospec Tech), were immunoadsorbed using onto plastic microwells (Costar Microtiter plates) using ELISA coating buffer (Alpha Diagnostic International, San Antonio, Tex.) for 24 hours at 4° C. After 24 hours, the plates were washed 5 times with ELISA wash solution (Quidel Corp), blocked with highly purified BSA for 1 hour, and washed 5 times again. PAP IC were incubated with either no peptide or with SEQ ID NO:20 for one hour. After an hour, the plates were washed 5 times with Quidel ELISA wash solution and then incubated with ABTS (Immunochem Corp.) for twenty minutes. The higher the $OD_{405\ nm}$, the higher the binding of DENV non-related immune complex (PAP-IC) to DENV NS1 protein. Results are shown in Table 6.

TABLE 6

| | | Amount of DENV NS1 coated onto wells | |
|---|---|---|---|
| | SEQ ID | 6 ng | 3 ng |
| No peptide inhibitor (+control) | — | 2.767 | 2.745 |
| APPDCAWHLGELVWCT | 20 | 0.220 | 0.286 |

Thus, SEQ ID NO:20 showed a marked ability to inhibit the binding of IC comprised PAP-IC to recombinant DENV NS1 coated plates.

Example 6

Inhibition of PAP-IC Binding to TNFα Coated Plates by SEQ ID NO:20

Highly purified recombinant TNF-α Sigma-Aldrich) was immunoadsorbed onto plastic microwells (Costar Microtiter plates) using ELISA coating buffer (Alpha Diagnostic International) for 24 hours at 4° C. After 24 hours, the plates were washed 5 times with ELISA wash solution (Quidel Corp), blocked with highly purified BSA for 1 hour, and washed 5 times. PAP IC were incubated with either no peptide or with peptide SEQ ID NO:20 for one hour. After an hour, the plates were washed 5 times with Quidel ELISA wash solution and then incubated with ABTS (Immunochem, Corp) for twenty minutes. The higher the $OD_{405\ nm}$, the higher the binding of TNF-α non-related immune complex (PAP-IC) to TNF-α was observed. Results are shown in Table 7.

TABLE 7

| Sample | SEQ ID | $OD_{405}$ |
|---|---|---|
| No peptide inhibitor (+control) | — | 3.180 |
| APPDCAWHLGELVWCT | 20 | 0.086 |

Thus, SEQ ID NO:20 showed a marked ability to inhibit the binding of IC comprised PAP-IC to recombinant TNFα coated plates.

Example 7

Demonstration of ADE in DENV(2) Infected In Vivo Mouse Model

The RAG2-/-γc-/-(RAG-hu) mouse model for dengue virus described above provides a unique research tool for addressing many important and timely questions about Dengue Virus infection and immunity (Kuruvilla et. al. (2007) *Virology* 369:143-152. RAG-hu mice are passively immunized with heterologous DENV IgG (i.e., neutralizing IgG for DENV 1; the sera could be from any DENV heterogous neutralizing DENV infection, such as DENV1 IgG and DENV2 infective virons or DENV2 IgG and DENV1 infective virons). The mice are passively immunized with anti-DENV 1 IgG, for example, and then inoculated with a lethal dose of, e.g., DENV 2 virus. A peptide having the sequence APPDCAWHLGELVWCT (SEQ ID NO:20) or XPPDCAWHLGELVWCT (SEQ ID NO:19) is administered i.p. at a daily dose of, e.g., 1 mg/kg, 10 mg/kg, 100 mg/kg and 1,000 mg/kg from the time of DENV infection. Gross clinical signs, temperature, etc., are monitored daily. Serum ELISA or RT-PCR for DENV NS1 or DENV replication and the presence of DENV NS1 IC. and DENV-IC are performed daily. A subset of DENV infected morbund mice are sacrificed daily and platelet counts, HCT/PCV, AST/ALT values are checked in addition to the measurements of DENV replication described above. An equal amount of DENV infected, APPD-CAWHLGELVWCT (SEQ ID NO:20) treated mice are sacrificed and examined as above for comparison purposes. At the end of the study, all immunological profiles and necropsy including biopsies of multiple DENV permissive tissues are carried out. A final analysis of ADE DENV infected mice is compared to ADE DENV infected, SEQ ID NO:20 treated mice.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting immune complex formation in a subject, said method comprising administering to said subject a composition comprising a purified polypeptide, said polypeptide comprising the amino acid sequence Xaa-Pro-Pro-Asp-Cys-Ala-Trp-His-Leu-Gly-Glu-Leu-Val-Trp-Cys-Thr (SEQ ID NO:19), wherein Xaa is any amino acid, and wherein said immune complex formation is associated with Antibody Dependent Enhancement (ADE) of Dengue Fever or infection by Dengue Virus (DENV), or contributes to the enhancement of a DENV infection.

2. The method of claim 1, wherein said immune complex formation is associated with infection by DENV, and wherein said infection by DENV is Dengue Hemorrhagic Fever (DHF) or Dengue Shock Syndrome (DSS).

3. The method of claim 1, wherein Xaa is Ala.

4. The method of claim 1, further comprising the step of monitoring said subject for one or more clinical, histiopathological or molecular characteristics of hemorrhagic fever.

5. The method of claim 4, wherein said one or more clinical, histiopathological, or molecular characteristics of hemorrhagic fever are selected from the group consisting of a decrease in platelets, hemoconcentration, or an increase in FcγR+ effector cells.

6. The method of claim 1, wherein said polypeptide comprises the amino acid sequence Ala-Pro-Pro-Asp-Cys-Ala-Trp-His-Leu-Gly-Glu-Leu-Val-Trp-Cys-Thr (SEQ ID NO:20).

* * * * *